(12) United States Patent
Bhat et al.

(10) Patent No.: US 8,669,285 B2
(45) Date of Patent: *Mar. 11, 2014

(54) SYNTHESIS, METHODS OF USING, AND COMPOSITIONS OF CYCLOALKYLMETHYLAMINES

(71) Applicant: Reviva Pharmaceuticals, Inc., San Jose, CA (US)

(72) Inventors: Laxminarayan Bhat, Cupertino, CA (US); Seema Rani Bhat, Cupertino, CA (US)

(73) Assignee: Reviva Pharmaceuticals, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/866,905

(22) Filed: Apr. 19, 2013

(65) Prior Publication Data

US 2013/0231386 A1 Sep. 5, 2013

Related U.S. Application Data

(60) Continuation of application No. 13/176,526, filed on Jul. 5, 2011, now Pat. No. 8,445,714, which is a division of application No. 11/856,670, filed on Sep. 17, 2007, now Pat. No. 7,989,500.

(60) Provisional application No. 60/825,868, filed on Sep. 15, 2006.

(51) Int. Cl.
*C07C 271/16* (2006.01)
*C07C 229/34* (2006.01)

(52) U.S. Cl.
USPC ............... 514/486; 514/539; 560/29; 560/39

(58) Field of Classification Search
None
See application file for complete search history.

(56) References Cited

U.S. PATENT DOCUMENTS 6,610,887 B2 * 8/2003 Senanayake et al. ......... 564/248

* cited by examiner

*Primary Examiner* — Kamal Saeed
(74) *Attorney, Agent, or Firm* — Perkins Coie LLP; Viola T. Kung

(57) ABSTRACT

The present invention provides novel cycloalkylmethylamine analogs, and methods of preparing cycloalkylmethylamine analogs. The present invention also provides methods of using cycloalkylmethylamine analogs and compositions of cycloalkylmethylamine analogs. The pharmaceutical compositions of the compounds of the present invention can be advantageously used for treating and/or preventing obesity and obesity related co-morbid indications.

20 Claims, No Drawings

SYNTHESIS, METHODS OF USING, AND COMPOSITIONS OF CYCLOALKYLMETHYLAMINES

This application is a continuation application of U.S. application Ser. No. 13/176,526, filed Jul. 5, 2011; which is a divisional application of U.S. application Ser. No. 11/856,670, filed Sep. 17, 2007, now U.S. Pat. No. 7,989,500; which claims the benefit of U.S. Provisional Application No. 60/825,868, filed Sep. 15, 2006. The above-identified applications are incorporated herein by reference in their entireties.

1. FIELD OF THE INVENTION

The present invention relates to cycloalkylmethylamines, synthesis of cycloalkylmethylamines and methods of using cycloalkylmethylamines for the pharmacological treatment of obesity and obesity related co-morbid indications.

2. BACKGROUND OF THE INVENTION

Obesity is a chronic disease that affects millions of people across the world especially in the developed countries. It is defined by excess body fat and is generally measured by calculating a person's BMI (body mass index). If a person's BMI is 30 or above, he or she considered to be obese. Obesity can cause a number of health problems either directly or indirectly, such as, for example, type 2 diabetes, coronary heart disease, high blood triglycerides, high blood pressure and stroke. Obesity also raises risk of certain types of cancer. Obese men are more likely than normal-weight peers to die from cancer of the colon, rectum, and prostate. Obese women are more likely than non-obese women to die from cancer of the gallbladder, breast, uterus, cervix and ovaries. Death from some cancers may be more likely because obesity makes the cancers harder to detect in the early stages (for example, the initial small lump of breast cancer may not be felt in an obese woman). Recent studies show obesity increases the risk of Alzheimer's-type dementia. Other disease and health problems linked to obesity include: gallbladder disease, gallstones, osteoarthritis, gout or joint pain, sleep apnea, psychological and social problems.

Obesity is caused by multiple factors, the primary factor being genetics which is the one factor relating to obesity over which individuals have no control. Other important factors involved in obesity are: the mechanisms of fat storage; the balance between energy intake and energy expenditure; an individual's life style: eating habits and exercise; and psychological, cultural and socioeconomic influences. Despite the seeming inexorable progression of this disease, there have been limited advances in the pharmacotherapy of this condition. Drugs to treat obesity can be divided into three groups: those that reduce food intake or appetite suppressants; those that alter metabolism or block the absorption of fat; and those that increase thermogenesis. Currently, there are only two drugs approved by the FDA for the long-term treatment of obesity and they are fat absorption blocker orlistat (XENICAL®) and the appetite suppressant sibutramine (MERIDIA®). The only thermogenic drug combination that has been tested is ephedrine and caffeine, but this treatment has not been approved by regulatory agencies.

The fat absorption blocker, orlistat works in the gastrointestinal tract by blocking an enzyme that is needed to digest fat. Instead of being absorbed from the intestine, up to one-third of the fat that a person consumes is excreted in the stool. In addition, orlistat blocks the absorption of needed fat-soluble vitamins A, D, E, and K, as well as beta-carotene. This is one of the major limitations of this drug for the long term use in the treatment of obesity. Most commonly reported side effects of orlistat are bloating, diarrhea and oily stools.

In the appetite suppressant category, a few noradrenergic and serotonergic drugs belong to a family of 2-arylethylamines are currently available in the market for the treatment of obesity. The noradrenergic agents such as phenylpropanolamine, (ACUTRIM®, DEXATRIM®), diethylpropion (TENUATE®), and phentermine (FASTIN®, IONAMIN®) are approved for the short-term treatment of obesity. Whereas, noradrenergic and serotonergic agent sibutramine (MERIDIA®) is the only drug currently approved for the long-term treatment of obesity in the appetite suppressant category. Sibutramine has cyclobutanemethylamine backbone and it is this backbone mainly responsible for its unique pharmacological properties.

In the last 10 years, a number of reports have been published on the possible use of sibutramine, either alone or in combination with other therapeutic agents, for the treatment and/or prevention of a variety diseases and/or disorders in addition to obesity (see, Montana, J. G. International Application Publication No. WO 2004/058237; Lulla, A. et al., International Application Publication No. WO 2004/096202; Jerussi, T. P. et al., International Application Publication No. WO 02/060424; Senanayake, C. H. et al., International Application Publication No. WO 01/51453; Heal, D. J. International Application Publication No. WO 01/00205; Birch, A. M. et al., International Application Publication No. WO 01/00187; Mueller, P. International Application Publication No. WO 00/32178; Bailey, C. International Application Publication No. WO 98/11884; Kelly, P. International Application Publication No. WO 98/13034). For examples: treatment of nausea, emesis, and related conditions; cognitive dysfunctions; eating disorders; weight gain; irritable bowel syndrome; obsessive compulsive disorders; platelet adhesion; apnea, affective disorders such as attention deficit disorders, depression, and anxiety; male and female sexual function disorders; restless leg syndrome; osteoarthritis; substance abuse including nicotine and cocaine addiction; narcolepsy; pain such as neuropathic pain, diabetic neuropathy, and chronic pain; migraines; cerebral function disorders; chronic disorders such as premenstrual syndrome; and incontinence.

In general, sibutramine has a number of therapeutic benefits because of its unique pharmacological properties. However, sibutramine's therapeutic use for the treatment of obesity, and other diseases and disorders is currently not fully utilized because of certain limitations and adverse side effects associated with the drug. The major adverse events reported, in some cases life threatening, include increase in blood pressure and the side effects derived from the drug-drug interactions, for example, serotonin syndrome. The majority of these adverse events are, to some extent, metabolism-based. Sibutramine exerts its pharmacological actions predominantly via its secondary ($M_1$) and primary ($M_2$) amine metabolites. Sibutramine is metabolized in the liver principally by the cytochrome P450 (3A4) isozymes, to desmethyl metabolites, $M_1$ and $M_2$. These active metabolites are further metabolized by hydroxylation and conjugation to pharmacologically inactive metabolites, $M_5$ and $M_6$. The elimination half-lives of therapeutically active primary and secondary metabolites $M_1$ and $M_2$ are 14 and 16 hours, respectively. It is evident from a number literature reports that cytochrome P450 mediated metabolism and the long half lives of active metabolites ($M_1$ and $M_2$) are mainly responsible for adverse events such as increased pressure and other side effects derived from drug-drug interactions of sibutramine.

Therefore, there is a need and great demand for safer and effective next generation appetite suppressants for the treatment of obesity. An ideal drug in this class should have potent appetite suppressant activity, a proven effect on fat loss, be well tolerated during acute and chronic administration and have alleviated side effects when compared to sibutramine and phentermine.

3. SUMMARY OF THE INVENTION

The present invention is directed towards compositions of novel cycloalkylmethylamine analogs and the use of the compositions for the treatment of obesity and related co-morbid conditions. The present invention provides methods for synthesizing such cycloalkylmethylamine analogs. The present invention also provides methods for using cycloalkylmethylamine analogs, and pharmaceutical composition of cycloalkylmethylamine analogs for treating or preventing obesity and co-morbid diseases and/or disorders.

The compounds of the subject invention provide next generation noradrenergic and serotonergic active appetite suppressants, and are particularly effective and safe for the treatment of obesity and co-morbid diseases and/or disorders. They are advantageous because of their favorable metabolic, pharmacokinetics and pharmacological profiles. Specifically, these compounds are primarily metabolized by hydrolytic enzymes not by cytochrome P450 enzymes. These compounds have a highly predictable pharmacokinetic profile and are particularly advantageous because they reduce systemic exposure to the active drug.

In one aspect, the present invention provides cycloalkylmethylamine derivatives comprising compounds of structural Formula (I):

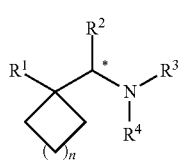

Formula (I)

or a pharmaceutically acceptable salts, hydrates or solvates thereof provided that the compounds of the invention comprise a soft-moiety conjugated directly or via a spacer on one of the substituents $R^1$, $R^2$, and $R^3$; wherein: n is 0, 1, 2, 3, 4, or 5;

$R^1$ and $R^2$ are independently selected to be hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, or substituted heteroarylalkyl, or optionally $R^1$ and $R^2$ together with the atoms to which $R^1$ and $R^2$ are attached, form a cycloalkyl, substituted cycloalkyl, cycloheteroalkyl or substituted cycloheteroalkyl ring which is optionally fused to an aryl, substituted aryl, heteroaryl, substituted heteroaryl, cycloalkyl, substituted cycloalkyl, cycloheteroalkyl or substituted cycloheteroalkyl ring;

$R^3$ can be selected to be hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, or substituted heteroarylalkyl; and $R^4$ can be selected to be hydrogen, alkyl, or substituted alkyl.

4. DETAILED DESCRIPTION OF THE INVENTION

This invention provides compounds, pharmaceutical compositions and methods for pharmacological treatment of obesity and related co-morbid diseases and/or disorders. This invention also provides methods for synthesis of novel appetite suppressants which are predominantly metabolized by hydrolytic enzymes. However, prior to describing this invention in further detail, the following terms will be first defined.

4.1 Definitions

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Definition of standard chemistry terms may be found in reference works, including Carey and Sundberg (1992) "Advanced Organic Chemistry $3^{rd}$ Ed." Vols. A and B, Plenum Press, New York. The practice of the present invention will employ, unless otherwise indicated, conventional methods of mass spectroscopy, protein chemistry, biochemistry, recombinant DNA techniques and pharmacology, within the skill of the art. The compositions and formulations described herein can be practiced employing the pharmaceutically acceptable excipients and salts available in *Remington's Pharmaceutical Sciences*, 18th Edition (Easton, Pa.: Mack Publishing Company, 1990).

"Compounds of the invention" refers to compounds encompassed by structural Formulae (I) to (IV) disclosed herein, and includes any specific compounds within these Formulae whose structure is disclosed herein. The compounds of the invention may be identified either by their chemical structure and/or chemical name. When the chemical structure and chemical name conflict, the chemical structures is determinative of the identity of the compound. The compounds of the invention may contain one or more chiral centers and/or double bonds and therefore, may exist as stereoisomers, such as double-bond isomers (i.e., geometric isomers), enantiomers or diastereoisomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds of the invention may also exist in several tautomeric forms including the enol form, the keto form and mixtures thereof. Accordingly, the chemical structures depicted herein encompass all possible tautomeric forms of the illustrated compounds. The compounds of the invention also include isotopically labeled compounds where one or more atoms have an atomic mass different from the atomic mass of conventionally found in nature. Examples of isotopes that may be incorporated into the compounds of the invention include, but are not limited to $^2H$, $^3H$, $^{13}C$, $^{15}N$, $^{18}O$, $^{17}O$, $^{31}P$, $^{32}P$, $^{35}S$, $^{18}F$ and $^{36}Cl$. Further, it should be understood, when partial structures of the compounds of the invention are illustrated, that brackets of dashes indicate the point of attachment of the partial structure to the rest of the molecule.

"Composition of the invention" refers to at least one compound of the invention and a pharmaceutically acceptable vehicle, with which the compound is administered to a patient. When administered to a patient, the compounds of the invention are administered is isolated form, which means separated from a synthetic organic reaction mixture.

"Alkyl" refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to methyl; ethyls such as ethanyl, ethenyl, ethynyl; propyls such as propan-1-yl, propan-2yl, cyclopropan-1-yl, prop-1-en-1-yl, prop-1-en-2-yl, prop-2-en-1-yl(allyl), cycloprop-1-en-1yl, cycloprop-2-en-1yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" specifically intended to include radicals having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl," are used. Preferably, an alkyl group comprises from 1-20 carbon atoms, more preferably, from 1 to 10 carbon atoms.

"Alkanyl" refers to a saturated branched, straight-chain or cyclic alkyl radical derived by the removal of one hydrogen atom from a single carbon atom of a parent alkane. Typical alkanyl groups include but are not limited to, methanyl; ethanyl; propanyls such as propan-1-yl, propan-2-yl(isopropyl), cyclopropan-1-yl, etc.; butanyls such as butan-1-yl, butan-2-yl(sec-butyl), 2-methyl-propan-1-yl(isobutyl), 2-methyl-propan-2-yl(t-butyl), cyclobutan-1-yl, etc.; and the like.

"Alkenyl" refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl(allyl), prop-2-en-2-yl, cycloprop-1-en-1-yl; cycloprop-2-en-1-yl; butenyls such as but-1-en-1-yl, but-1-en-2-yl, 2-methy-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Acyl" refers to a radical —C(O)R, where R is hydrogen, alkyl, cycloalkyl, cycloheteroalkyl, aryl, arylalkyl, heteroalkyl, heteroaryl, heteroarylalkyl, as defined herein that may be optionally substituted as defined herein. Representative examples include, but are not limited to formyl, acetyl, cyclohexylcarbonyl, cyclohexylmethylcarbonyl, benzoyl, benzylcarbonyl and the like.

"Acyloxyalkyloxycarbonyl" refers to a radical —C(O)OCR'R"OC(O)R'", where R', R", and R'" are each independently hydrogen, alkyl, cycloalkyl, cycloheteroalkyl, aryl, arylalkyl, heteroalkyl, heteroaryl, heteroarylalkyl, as defined herein that may be optionally substituted as defined herein. Representative examples include, but not limited to —C(O)OCH$_2$OC(O)CH$_3$, —C(O)OCH$_2$OC(O)CH$_2$CH$_3$, —C(O)OCH(CH$_3$)OC(O)CH$_2$CH$_3$, —C(O)OCH(CH$_3$)OC(O)C$_6$H$_5$ and the like.

"Acylalkyloxycarbonyl" refers to a radical —C(O)OCR'R"C(O)R'", where R', R", and R'" are each independently hydrogen, alkyl, cycloalkyl, cycloheteroalkyl, aryl, arylalkyl, heteroalkyl, heteroaryl, heteroarylalkyl, as defined herein that may be optionally substituted as defined herein. Representative examples include, but not limited to —C(O)OCH$_2$C(O)CH$_3$, —C(O)OCH$_2$C(O)CH$_2$CH$_3$, —C(O)OCH(CH$_3$)C(O)CH$_2$CH$_3$, —C(O)OCH(CH$_3$)C(O)C$_6$H$_5$ and the like.

"Acyloxyalkyloxycarbonylamino" refers to a radical —NRC(O)OCR'R"OC(O)R'", where R, R', R", and R'" are each independently hydrogen, alkyl, cycloalkyl, cycloheteroalkyl, aryl, arylalkyl, heteroalkyl, heteroaryl, heteroarylalkyl, as defined herein that may be optionally substituted as defined herein. Representative examples include, but not limited to —NHC(O)OCH$_2$OC(O)CH$_3$, —NHC(O)OCH$_2$OC(O)CH$_2$CH$_3$, —NHC(O)OCH(CH$_3$)OC(O)CH$_2$CH$_3$, —NHC(O)OCH(CH$_3$)OC(O)C$_6$H$_5$ and the like.

"Acylalkyloxycarbonylamino" refers to a radical —NRC(O)OCR'R"C(O)R'", where R, R', R", and R'" are each independently hydrogen, alkyl, cycloalkyl, cycloheteroalkyl, aryl, arylalkyl, heteroalkyl, heteroaryl, heteroarylalkyl, as defined herein that may be optionally substituted as defined herein. Representative examples include, but not limited to —NHC(O)OCH$_2$C(O)CH$_3$, —NHC(O)OCH$_2$C(O)CH$_2$CH$_3$, —NHC(O)OCH(CH$_3$)C(O)CH$_2$CH$_3$, —NHC(O)OCH(CH$_3$)C(O)C$_6$H$_5$ and the like.

"Acylamino" refers to "Amide" as defined herein.

"Alkylamino" means a radical —NHR where R represents an alkyl, or cycloalkyl group as defined herein that may be optionally substituted as defined herein. Representative examples include, but are not limited to, methylamino, ethylamino, 1-methylethylamino, cyclohexylamino and the like.

"Alkoxy" refers to a radical —OR where R represents an alkyl, or cycloalkyl group as defined herein that may be optionally substituted as defined herein. Representative examples include, but are not limited to methoxy, ethoxy, propoxy, butoxy, cyclohexyloxy and the like.

"Alkoxycarbonyl" refers to a radical —C(O)-alkoxy where alkoxy is as defined herein.

"Alkoxycarbonylalkoxy" refers to a radical —OCR'R"C(O)-alkoxy where alkoxy is as defined herein. Similarly, where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted as defined herein. Representative examples include, but are not limited to —OCH$_2$C(O)OCH$_3$, —OCH$_2$C(O)OCH$_2$CH$_3$, —OCH(CH$_3$)C(O)OCH$_2$CH$_3$, —OCH(C$_6$H$_5$)C(O)OCH$_2$CH$_3$, —OCH(CH$_2$C$_6$H$_5$)C(O)OCH$_2$CH$_3$, —OC(CH$_3$)(CH$_3$)C(O)OCH$_2$CH$_3$, and the like.

"Alkoxycarbonylalkylamino" refers to a radical —NRCR'R"C(O)-alkoxy where alkoxy is as defined herein. Similarly, where R, R', R' and R" are each independently hydrogen, alkyl, cycloalkyl, cycloheteroalkyl, aryl, arylalkyl, heteroalkyl, heteroaryl, heteroarylalkyl, as defined herein that may be optionally substituted as defined herein. Representative examples include, but are not limited to —NHCH$_2$C(O)OCH$_3$, —N(CH$_3$)CH$_2$C(O)OCH$_2$CH$_3$, —NHCH(CH$_3$)C(O)OCH$_2$CH$_3$, —NHCH(C$_6$H$_5$)C(O)OCH$_2$CH$_3$, —NHCH(CH$_2$C$_6$H$_5$)C(O)OCH$_2$CH$_3$, —NHC(CH$_3$)(CH$_3$)C(O)OCH$_2$CH$_3$, and the like.

"Alkylsulfonyl" refers to a radical —S(O)$_2$R where R is an alkyl, or cycloalkyl group as defined herein that may be optionally substituted as defined herein. Representative examples include, but are not limited to, methylsulfonyl, ethylsulfonyl, propylsulfonyl, butylsulfonyl, and the like.

"Alkylsulfinyl" refers to a radical —S(O)R where R is an alkyl, or cycloalkyl group as defined herein that may be optionally substituted as defined herein. Representative examples include, but are not limited to, methylsulfinyl, ethylsulfinyl, propylsulfinyl, butylsulfinyl, and the like.

"Alkylthio" refers to a radical —SR where R is an alkyl or cycloalkyl group as defined herein that may be optionally substituted as defined herein. Representative examples include, but are not limited to methylthio, ethylthio, propylthio, butylthio, and the like.

"Amide or Acylamino" refers to a radical —NR'C(O)R", where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted as defined herein. Representative examples include, but are not limited to, formylamino acetylamino, cyclohexylcarbonylamino, cyclohexylmethylcarbonylamino, benzoylamino, benzylcarbonylamino and the like.

"Amino" refers to the radical —NH$_2$

"Aryl" refers to a monovalent aromatic hydrocarbon radical derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorine, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleidene, pyrene, pyranthrene, rubicene, triphenylene, trinaphthalene, and the like. Preferable, an aryl group comprises from 6 to 20 carbon atoms, more preferably, between 6 to 12 carbon atoms.

"Arylalkyl" refers to an acyclic alkyl in which one of the hydrogen atoms bonded to a carbon atom, typically a terminal or sp$^3$ carbon atom, is replaced with an aryl group. Typically arylalkyl groups include, but not limited to, benzyl, 2-phenylethan-1-yl, 2-phenylethen-1-yl, naphthylmethyl, 2-naphthylethan-1-yl, 2-naphthylethene-1-yl, naphthobenzyl, 2-naphthophenylethan-1-yl and the like. Where specific alkyl moieties are intended, the nomenclature arylalkany, arylalkenyl and/or arylalkynyl is used. Preferably, an arylalkyl group is ($C_6$-$C_{30}$)arylalkyl, e.g., the alkanyl, alkenyl or alkynyl moiety of the arylalkyl group is ($C_1$-$C_{10}$) and the aryl moiety is ($C_6$-$C_{20}$), more preferably, an arylalkyl group is ($C_6$-$C_{20}$) arylalkyl, e.g., the alkanyl, alkenyl or alkynyl moiety of the arylalkyl group is ($C_1$-$C_8$) and the aryl moiety is ($C_6$-$C_{12}$).

"Arylalkoxy" refers to an —O-arylalkyl radical where arylalkyl is as defined herein that may be optionally substituted as defined herein.

"Arylalkoxycarbonylalkoxy" refers to a radical —OCR'R"C(O)-arylalkoxy where arylalkoxy is as defined herein. Similarly, where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted as defined herein. Representative examples include, but are not limited to —OCH$_2$C(O)OCH$_2$C$_6$H$_5$, —OCH(CH$_3$)C(O)O CH$_2$C$_6$H$_5$, —OCH(C$_6$H$_5$)C(O)O CH$_2$C$_6$H$_5$, —OCH(CH$_2$C$_6$H$_5$)C(O)OCH$_2$C$_6$H$_5$, —OC(CH$_3$)(CH$_3$)C(O)O CH$_2$C$_6$H$_5$, and the like.

"Arylalkoxycarbonylalkylamino" refers to a radical —NRCR'R"C(O)-arylalkoxy where arylalkoxy is as defined herein. Similarly, where R, R', R' and R" are each independently hydrogen, alkyl, cycloalkyl, cycloheteroalkyl, aryl, arylalkyl, heteroalkyl, heteroaryl, heteroarylalkyl, as defined herein that may be optionally substituted as defined herein. Representative examples include, but are not limited to —NHCH$_2$C(O)OCH$_2$C$_6$H$_5$, —N(CH$_3$)CH$_2$C(O)OCH$_2$C$_6$H$_5$, —NHCH(CH$_3$)C(O)OCH$_2$C$_6$H$_5$, —NHCH(C$_6$H$_5$)C(O)OCH$_2$C$_6$H$_5$, —NHCH(CH$_2$C$_6$H$_5$)C(O)OCH$_2$C$_6$H$_5$, —NHC(CH$_3$)(CH$_3$)C(O)OCH$_2$C$_6$H$_5$, and the like.

"Aryloxycarbonyl" refers to radical —C(O)—O-aryl where aryl is defined herein that may be optionally substituted as defined herein.

"Aryloxycarbonylalkoxy" refers to a radical —OCR'R"C(O)-aryloxy where aryloxy is as defined herein. Similarly, where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted as defined herein. Representative examples include, but are not limited to —OCH$_2$C(O)OC$_6$H$_5$, —OCH(CH$_3$)C(O)OC$_6$H$_5$, —OCH(C$_6$H$_5$)C(O)OC$_6$H$_5$, —OCH(CH$_2$C$_6$H$_5$)C(O)OC$_6$H$_5$, —OC(CH$_3$)(CH$_3$)C(O)OC$_6$H$_5$, and the like.

"Aryloxycarbonylalkylamino" refers to a radical —NRCR'R"C(O)-aryloxy where aryloxy is as defined herein. Similarly, where R, R', R' and R" are each independently hydrogen, alkyl, cycloalkyl, cycloheteroalkyl, aryl, arylalkyl, heteroalkyl, heteroaryl, heteroarylalkyl, as defined herein that may be optionally substituted as defined herein. Representative examples include, but are not limited to —NHCH$_2$C(O)OC$_6$H$_5$, —N(CH$_3$)CH$_2$C(O)OC$_6$H$_5$, —NHCH(CH$_3$)C(O)OC$_6$H$_5$, —NHCH(C$_6$H$_5$)C(O)OC$_6$H$_5$, —NHCH(CH$_2$C$_6$H$_5$)C(O)OC$_6$H$_5$, —NHC(CH$_3$)(CH$_3$)C(O)OC$_6$H$_5$, and the like.

"Carbamoyl" refers to the radical —C(O)N(R)$_2$ where each R group is independently, hydrogen, alkyl, cycloalkyl, cycloheteroalkyl, aryl, arylalkyl, heteroalkyl, heteroaryl, heteroarylalkyl, as defined herein that may be optionally substituted as defined herein.

"Carbamate" refers to a radical —NR'C(O)OR", where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted as defined herein. Representative examples include, but are not limited to, methylcarbamate (—NHC(O)OCH$_3$), ethylcarbamate (—NHC(O)OCH$_2$CH$_3$), benzylcarbamate (—NHC(O)OCH$_2$C$_6$H$_5$), and the like.

"Carbonate" refers to a radical —OC(O)OR, where R is alkyl, cycloalkyl, cycloheteroalkyl, aryl, arylalkyl, heteroalkyl, heteroaryl, heteroarylalkyl, as defined herein that may be optionally substituted as defined herein. Representative examples include, but are not limited to, methyl carbonate (—C(O)OCH$_3$), cyclohexyl carbonate (—C(O)OC$_6$H$_{11}$), phenyl carbonate (—C(O)OC$_6$H$_5$), benzyl carbonate (—C(O)OCH$_2$C$_6$H$_5$), and the like.

"Carboxy" means the radical —C(O)OH.

"Cyano" means the radical —CN.

"Cycloalkyl" refers to a substituted or unsubstituted cylic alkyl radical. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. In a preferred embodiment, the cycloalkyl group is ($C_3$-$C_{10}$) cycloalkyl, more preferably ($C_3$-$C_7$) cycloalkyl.

"Cycloheteroalkyl" refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, imidazolidine, morpholine, piperazine, piperidine, pyrazolidine, pyrrolidine, quinuclidine, and the like.

"Cycloheteroalkoxycarbonyl" refers to a radical —C(O)—OR where R is cycloheteroalkyl as defined herein.

"Dialkylamino" means a radical —NRR' where R and R' independently represent an alkyl or cycloalkyl group as defined herein. Representative examples include, but are not limited to dimethylamino, methylethylamino, di-(1-methylethyl)amino, (cyclohexyl)(methyl)amino, (cyclohexyl)(ethyl)amino, (cyclohexyl)(propyl)amino, and the like.

"Derived from a drug" refers to a fragment that is structurally related to such a drug. The structure of the fragment is identical to the drug except where a hydrogen atom attached to a heteroatom (N or O) has been replaced with a covalent bond to another group (typically, a promoiety). Note that when a drug is a salt form of a carboxylic, phosphonic or phosphoric acid, the corresponding structural fragment derived from such a drug is considered to derived from the protonated acid form.

"Drug" refers to a compound that exhibits therapeutic and/or prophylactic and/or diagnostic utility when administered in effective amounts to a patient or a mammal.

"Ester" refers to a radical —C(O)OR, where R is alkyl, substituted alkyl, cycloalkyl, substituted cycloalkyl, cycloheteroalkyl, substituted cycloheteroalkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl as defined herein. Representative examples include, but are not limited to, methyl ester (—C(O)OCH$_3$), cyclohexyl ester (—C(O)OC$_6$H$_{11}$), phenyl ester (—C(O)OC$_6$H$_5$), benzyl ester (—C(O)OCH$_2$C$_6$H$_5$), and the like.

"Halo" means fluoro, chloro, bromo, or iodo.

"Heteroalkoxy" means an —O-heteroalkyl radical where heteroalkyl is as defined herein.

"Heteroalkyl, Heteroalkanyl, Heteroalkenyl, Heteroalkynyl" refer to alkyl, alkanyl, alkenyl and alkynyl groups, respectively, in which one or more of the carbon atoms (and any associated hydrogen atoms) are each independently replaced with the same or different heteroatomic groups. Typical heteroatomic groups include, but are not limited to —O—, —S—, —O—O—, —S—S—, —OS—, —NR'—, =N—N=, —N=N—, —N=N—NR'—, —PH—, —P(O)$_2$—, —O—P(O)—, —S(O)—, —S(O)$_2$—, —SnH$_2$—, and the like, wherein R' is hydrogen, alkyl, substituted alkyl, cycloalkyl, substituted cycloalkyl, aryl or substituted aryl.

"Heteroaryl" refers to a monovalent heteroaromatic radical derived by the removal of one hydrogen atom from a single atom of a parent heteroaromatic ring system. Typical heteroaryl groups include, but are not limited to, groups derived from acridine, arsindole, carbazole, carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is between 5-20 membered heteroaryl, with 5-10 membered heteroaryl being particularly preferred. Preferred heteroaryl groups are those derived from thiophene, pyrrole, benzothiophene, benzofuran, indole, pyridine, quinoline, imidazole, oxazole and pyrazine.

"Heteroaryloxycarbonyl" refers to a radical —C(O)—OR where R is heteroaryl as defined.

"Heteroarylalkyl" refers to an acyclic alkyl radical in which one of the hydrogen atoms bonded to a carbon atom, typically a terminal or sp3 carbon atom, is replaced with a heteroaryl group. Where specific alkyl moieties are intended, the nomenclature heteroarylalkanyl, heteroarylalkenyl and/or heteroarylalkynyl is used. Preferably, the heteroarylalkyl radical is a 6-30 carbon membered heteroarylalkyl, e.g., the alkanyl, alkenyl or alkynyl moiety of the heteroarylalkyl is 1-10 membered and the heteroaryl moiety is a 5-20 membered heteroaryl, more preferably, a 6-20 membered heteroarylalkyl, e.g., the alkanyl, alkenyl or alkynyl moiety of the heteroarylalkyl is 1-8 membered and the heteroaryl moiety is a 5-12 membered heteroaryl.

"Hydroxy" means the radical —OH.

"Oxo" means the divalent radical =O.

As used herein, the term "patient" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. The term does not denote a particular age or gender.

"Pharmaceutically acceptable" means approved or approvable by a regulatory agency of the Federal or state government or listed in the U.S. Pharmacopoeia or other generally recognized pharmacopoeia for use in animals, and more particularly in humans.

"Pharmaceutically acceptable salt" refers to a salt of a compound of the invention, which is pharmaceutically acceptable and possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentane propionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2,2,2]-oct-2-ene-1-carboxylic acid, glucoheptonic acid, 3-phenylpropionic acid, trimethylacetic acid, tertiary butylacetic acid, laurylsulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Pharmaceutically acceptable vehicle" refers to a diluent, adjuvant, excipient or carrier with which a compound of the invention is administered.

"Phosphate" refers to a radical —OP(O)(OR')(OR"), where R' and R" are each independently hydrogen, alkyl, cycloalkyl, cycloheteroalkyl, aryl, arylalkyl, heteroalkyl, heteroaryl, heteroarylalkyl, as defined herein that may be optionally substituted as defined herein.

"Preventing" or "Prevention" refers to a reduction in risk of acquiring a disease or disorder (i.e., causing at least one of the clinical symptoms of the disease not to develop in a patient that may be exposed to or preposed to the disease but does not yet experience or display symptoms of the disease).

"Prodrug" refers to a derivative of a drug molecule that requires a transformation within the body to release the active drug. Prodrugs are frequently (though not necessarily) pharmacologically inactive until converted to the parent drug.

"Promoiety" refers to a form of protecting group that when used to mask a functional group within a drug molecule converts the drug into a prodrug. Typically, the promoiety will be attached to the drug via bond(s) that are cleaved by enzymatic or non-enzymatic means in vivo.

"Protecting group" refers to a group of atoms that when attached to a reactive group in a molecule masks, reduces or prevents that reactivity. Examples of protecting groups can be found in Green et al., "Protective Groups in Organic Chemistry", (Wiley, 2$^{nd}$ ed. 1991) and Harrison et al., "Compendium of Synthetic Organic Methods", vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilylethanesulfonyl ("SES"), trityl and substituted trityl groups, allyloxycarbonyl, 9-fluorenylmethyloxycarbonyl ("FMOC"), nitroveratryloxycarbonyl ("NVOC") and the like. Representative hydroxyl protecting groups include, but are not limited to, those where the hydroxyl group is either acylated or alkylated such as benzyl, and trialkylsilyl ethers and allyl ethers.

"Racemate" refers to an equimolar mixture of enantiomers of a chiral molecule.

"Soft moiety" refers to a moiety that contain hydrolysable bonds that can be incorporated into compounds according to the invention include but not limited are amide, ester, carbonate, phosphate, sulfate, urea, urethane, glycoside, or other bonds that can be cleaved by hydrolases.

"Spacer" refers to a substituent like O, S, alkyl, substituted alkyl, acyl, acylamino, alkoxy, alkylamino, alkylthio, amino, aryl, substituted aryl, arylalkyl, substituted arylalkyl, arylalkoxy, substituted arylalkoxy, carboxy, cycloalkyl, substituted cycloalkyl, cycloheteroalkyl, substituted cycloheteroalkyl, and hydroxy.

"Substituted" refers to a group in which one or more hydrogen atoms are each independently replaced with the same or different substituents(s). Typical substituents include, but are not limited to, —X, —R$^{54}$, —O$^-$, =O, —OR$^{54}$, —SR$^{54}$, —S, =S, —NR$^{54}$R$^{55}$, =NR$^{54}$, —CX$_3$, —CF$_3$, —CN, —OCN, —SCN, —NO, —NO$_2$, =N$_2$, —N$_3$, —S(O)$_2$O$^-$, —S(O)$_2$OH, —S(O)$_2$OR$^{54}$, —OS(O)$_2$O$^{31}$, —OS(O)$_2$R$^{54}$, —P(O)(O—)$_2$, —P(O)(OR$^{14}$)(O$^{31}$), —OP(O)(OR$^{54}$)(OR$^{55}$), —C(O)R$^{54}$, —C(S)R$^{54}$, —C(O)OR$^{54}$, —C(O)NR$^{54}$R$^{55}$, —C(O)O$^-$, —C(S)OR$^{54}$, —NR$^{56}$C(O)NR$^{54}$R$^{55}$, —NR$^{56}$C(S)NR$^{54}$R$^{55}$, —NR$^{57}$C(NR$^{56}$)NR$^{54}$R$^{55}$, and —C(NR$^{56}$)NR$^{54}$R$^{55}$, where each X is independently a halogen; each R$^{54}$, R$^{55}$, R$^{56}$ and R$^{57}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl, —NR$^{58}$R$^{59}$, —C(O)R$^{58}$ or —S(O)$_2$R$^{58}$ or optionally R$^{58}$ and R$^{59}$ together with the atom to which they are both attached form a cycloheteroalkyl or substituted cycloheteroalkyl ring; and R$^{58}$ and R$^{59}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl.

"Sulfate" refers to a radical —OS(O)(O)OR, where R is hydrogen, alkyl, cycloalkyl, cycloheteroalkyl, aryl, arylalkyl, heteroalkyl, heteroaryl, heteroarylalkyl, as defined herein that may be optionally substituted as defined herein.

"Thio" means the radical —SH.

"Treating" or "Treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the patient. In yet another embodiment, "treating" or "treatment" refers to inhibiting the disease or disorder, either physically (e.g., stabilization of a discernible symptom), physiologically, (e.g., stabilization of a physical parameter), or both. In yet another embodiment, "treating" or "treatment" refers to delaying the onset of the disease or disorder.

"Therapeutically effective amount" means the amount of a compound that, when administered to a patient for treating a disease, is sufficient to effect such treatment for the disease. The "therapeutically effective amount" will vary depending on the compound, the disease and is severity and the age, weight, etc., of the patient to be treated, and can be determined by one of skill in the art without undue experimentation.

Reference now will be made in detail to preferred embodiments of the invention. While the invention will be described in conjunction with preferred embodiments, it will be understood that it is not intended to limit the invention to those preferred embodiments. To the contrary, it is intended to cover alternatives, modifications, and equivalents as may be included within the spirit and scope of the invention as defined by the appended claims

4.2 Compounds of the Invention

The present invention provides cycloalkylmethylamine derivatives comprising compounds of structural Formula (I):

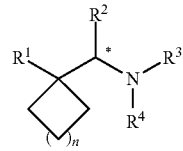

Formula (1)

or a pharmaceutically acceptable salt, hydrate or solvate thereof, provided that the compounds of the invention comprise a soft-moiety conjugated directly or via a spacer on one of the substituents R$^1$, R$^2$, or R$^3$; wherein n is 0, 1, 2, 3, 4, or 5; R$^1$ and R$^2$ are independently selected to be hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, or substituted heteroarylalkyl, or optionally R$^1$ and R$^2$ together with the atoms to which R$^1$ and R² are attached, form a cycloalkyl, substituted cycloalkyl, cycloheteroalkyl or substituted cycloheteroalkyl ring which is optionally fused to an aryl, substituted aryl, heteroaryl, substituted heteroaryl, cycloalkyl, substituted cycloalkyl, cycloheteroalkyl or substituted cycloheteroalkyl ring; R³ can be selected to be hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, or substituted heteroarylalkyl; and R⁴ can be selected to be hydrogen, alkyl, or substituted alkyl. The carbon with the * denotes a carbon capable of being optically active. The compounds of the invention includes both R and S compounds.

In one aspect of the invention, compounds of structural Formula (II) are described,

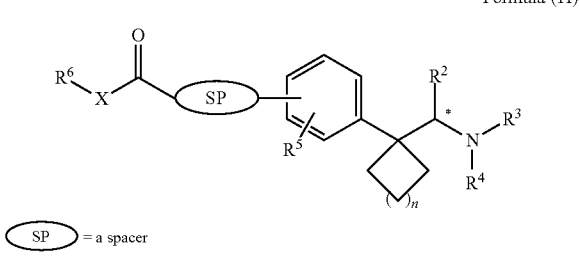

Formula (II)

wherein n is 0, 1, 2, 3, 4, or 5;
"SP" refers to a spacer;
X can be O, S, or NR₁₃ where R₁₃ can be H, or lower alkyl;
R² can be hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, or optionally R² and either R⁵ or "SP" (spacer), together with the atoms to which R² and R⁵ or "SP" are attached, form a cycloalkyl, substituted cycloalkyl, cycloheteroalkyl or substituted cycloheteroalkyl ring which is optionally fused to an aryl, substituted aryl, heteroaryl, substituted heteroaryl, cycloalkyl, substituted cycloalkyl, cycloheteroalkyl or substituted cycloheteroalkyl ring;
R³ can be hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, or substituted heteroarylalkyl;
R⁴ can be hydrogen, alkyl, or substituted alkyl;
R⁵ can be hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl; preferably acyl, acylamino, alkoxy, alkoxycarbonyl, alkoxycarbonylalkoxy, alkoxycarbonylalkylamino, alkylamino, alkylsulfonyl, alkylsulfinyl, alkylthio, amino, arylalkoxy, arylalkoxycarbonylalkoxy, arylalkoxycarbonylalkylamino, aryloxycarbonyl, aryloxycarbonylalkoxy, carbamoyl, carbamate, carboxy, cyano, dialkylamino, ester, halo, heteroalkoxy, hydroxy; or phosphate; heteroaryl, substituted heteroaryl, heteroarylalkyl, or substituted heteroarylalkyl; and
R⁶ can be hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, or substituted heteroarylalkyl.

In another aspect of the invention, compounds comprise structural Formula (III),

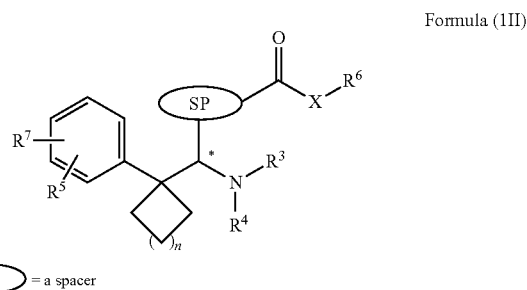

Formula (III)

wherein n is 0, 1, 2, 3, 4, or 5;
"SP" refers to a spacer;
X can be O, S, or NR₁₃ where R₁₃ can be H, or lower alkyl;
R³ can be hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, or substituted heteroarylalkyl;
R⁴ can be hydrogen, alkyl, or substituted alkyl;
R⁵ can be hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl; preferably acyl, acylamino, alkoxy, alkoxycarbonyl, alkoxycarbonylalkoxy, alkoxycarbonylalkylamino, alkylamino, alkylsulfonyl, alkylsulfinyl, alkylthio, amino, arylalkoxy, arylalkoxycarbonylalkoxy, arylalkoxycarbonylalkylamino, aryloxycarbonyl, aryloxycarbonylalkoxy, carbamoyl, carbamate, carboxy, cyano, dialkylamino, ester, halo, heteroalkoxy, hydroxy or phosphate;
R⁷ can be hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl; preferably acyl, acylamino, alkoxy, alkoxycarbonyl, alkoxycarbonylalkoxy, alkoxycarbonylalkylamino, alkylamino, alkylsulfonyl, alkylsulfinyl, alkylthio, amino, arylalkoxy, arylalkoxycarbonylalkoxy, arylalkoxycarbonylalkylamino, aryloxycarbonyl, aryloxycarbonylalkoxy, carbamoyl, carbamate, carboxy, cyano, dialkylamino, ester, halo, heteroalkoxy, hydroxy or phosphate; or optionally R⁵ and R⁷ together with the atoms to which R⁵ and R⁷ are attached, form a cycloalkyl, substituted cycloalkyl, cycloheteroalkyl or substituted cycloheteroalkyl ring which is optionally fused to an aryl, substituted aryl, heteroaryl, substituted heteroaryl, cycloalkyl, substituted cycloalkyl, cycloheteroalkyl or substituted cycloheteroalkyl ring; and
R⁶ can be hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, or substituted heteroarylalkyl.

In yet another aspect, the invention provides compounds of structural Formula (IV),

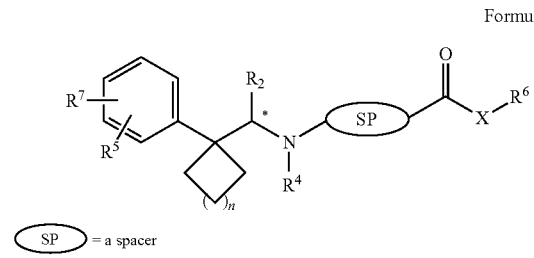

Formula (IV)

SP = a spacer wherein n can be 0, 1, 2, 3, 4, or 5;
"SP" refers to a spacer;
X can be O, S, or $NR_{13}$ where $R_{13}$ can be H, or lower alkyl;
$R^2$ can be hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, or optionally $R^2$ and either $R^5$ or $R^8$ together with the atoms to which $R^2$ and $R^5$ or $R^8$, form a cycloalkyl, substituted cycloalkyl, cycloheteroalkyl or substituted cycloheteroalkyl ring which is optionally fused to an aryl, substituted aryl, heteroaryl, substituted heteroaryl, cycloalkyl, substituted cycloalkyl, cycloheteroalkyl or substituted cycloheteroalkyl ring;
$R^4$ can be hydrogen, alkyl, or substituted alkyl;
$R^5$ can be hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl; acyl, acylamino, alkoxy, alkoxycarbonyl, alkoxycarbonylalkoxy, alkoxycarbonylalkylamino, alkylamino, alkylsulfonyl, alkylsulfinyl, alkylthio, amino, arylalkoxy, arylalkoxycarbonylalkoxy, arylalkoxycarbonylalkylamino, aryloxycarbonyl, aryloxycarbonylalkoxy, carbamoyl, carbamate, carboxy, cyano, dialkylamino, ester, halo, heteroalkoxy, hydroxy, or phosphate; or optionally $R^5$ and $R^8$ together with the atoms to which $R^5$ and $R^8$, form a cycloalkyl, substituted cycloalkyl, cycloheteroalkyl or substituted cycloheteroalkyl ring which is optionally fused to an aryl, substituted aryl, heteroaryl, substituted heteroaryl, cycloalkyl, substituted cycloalkyl, cycloheteroalkyl or substituted cycloheteroalkyl ring;
$R^8$ can be hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl; preferably acyl, acylamino, alkoxy, alkoxycarbonyl, alkoxycarbonylalkoxy, alkoxycarbonylalkylamino, alkylamino, alkylsulfonyl, alkylsulfinyl, alkylthio, amino, arylalkoxy, arylalkoxycarbonylalkoxy, arylalkoxycarbonylalkylamino, aryloxycarbonyl, aryloxycarbonylalkoxy, carbamoyl, carbamate, carboxy, cyano, dialkylamino, ester, halo, heteroalkoxy, hydroxy or phosphate; or optionally $R^5$ and $R^8$ together with the atoms to which $R^5$ and $R^8$ are attached, form a cycloalkyl, substituted cycloalkyl, cycloheteroalkyl or substituted cycloheteroalkyl ring which is optionally fused to an aryl, substituted aryl, heteroaryl, substituted heteroaryl, cycloalkyl, substituted cycloalkyl, cycloheteroalkyl or substituted cycloheteroalkyl ring; and $R^6$ can be hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, or substituted heteroarylalkyl.

The compounds of this invention described herein can have one or more of the following characteristics or properties:
1. Compounds of the invention can have dopamine, norepinephrine and serotonin reuptake inhibitory properties;
2. Compounds according to the invention contain at least one hydrolysable bond that can be cleaved non-oxidatively by hydrolytic enzymes;
3. The primary metabolites of compounds of this invention results from the non-oxidative metabolism of the compounds;
4. The primary metabolites, regardless of the electrophysiological properties of the parent drug, has, or have, negligible inhibitory activity at the IKr (HERG) channel at the normal therapeutic concentration of the parent drug in plasma (e.g. the concentration of the metabolite must be at least five times higher than the normal therapeutic concentration of the parent compound before activity at the IKr channel is observed);
5. Compounds of the invention, as well as the metabolites thereof, do not cause metabolic drug-drug interaction (DDI) when co-administered with other drugs;
6. Compounds of the invention, as well as metabolites thereof, do not elevate liver function test (LFT) values when administered alone;
7. Oral bioavailability of the compounds is consistent with oral administration using standard pharmacological oral formulations; however, the compounds, and compositions thereof, can also be administered using any delivery system that produces constant and controllable blood levels overt time.

In some embodiments, the subject invention provides compounds having any two or more of the above identified characteristics or properties. Other embodiments provide for compounds having at least any three or more of the above identified properties or characteristics. In another embodiment, the compounds, and compositions thereof, have any combination of four to seven of the above identified characteristics or properties. In a preferred embodiment the compounds of the invention have all seven characteristics or properties.

Preferably, the primary metabolites of the inventive compounds, regardless of the electrophysiological properties of the parent drug, have negligible inhibitory activity at the IKr (HERG) channel at normal therapeutic concentrations of the drug in plasma. In other words, the concentration of the metabolite preferably is at least five times higher than the normal therapeutic concentration of the parent compound before activity at the IKr channel is observed. Preferably, the concentration of the metabolite is at least ten times higher than the normal therapeutic concentration of the parent compound before activity at the IKr channel is observed.

Compounds according to the invention are primarily metabolized by endogenous hydrolytic enzymes via hydrolysable bonds engineered into their structures. The primary metabolites resulting from this metabolic pathway are water soluble and do not have, or show a reduced incidence of, DDI when administered with other medications (drugs). Non-limiting examples of hydrolysable bonds that can be incorporated into compounds according to the invention include amide, ester, carbonate, phosphate, sulfate, urea, urethane, glycoside, or other bonds that can be cleaved by hydrolases.

Additional modifications of the compounds disclosed herein can readily be made by those skilled in the art. Thus, analogs and salts of the exemplified compounds are within the scope of the subject invention. With knowledge of the compounds of the subject invention skilled chemists can use known procedures to synthesize these compounds from available substrates. As used in this application, the term "analogs" refers to compounds which are substantially the same as another compound but which may have been modified by, for example, adding additional side groups. The term "analogs" as used in this application also may refer to compounds which are substantially the same as another compound but which have atomic or molecular substitution at certain locations in the compound.

The subject invention further pertains to enantiomerically isolated compounds, and compositions comprising the compounds. The isolated enantiomeric forms of the compounds of the invention are substantially free from one another (i.e., in enantiomeric excess). In other words, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. In one embodiment of the invention, the isolated enantiomeric compounds are at least about 80% enantiomeric excess. In a preferred embodiment, the compounds are in at least about 90% enantiomeric excess. In a more preferred embodiment, the compounds are in at least about 95% enantiomeric excess. In an even more preferred embodiment, the compounds are in at least about 97% enantiomeric excess. In a most preferred embodiment, the compounds are in at least 99% or greater than 99% enantiomeric excess.

4.3 Synthesis of the Compounds of the Invention

The compounds of the invention can be obtained via the synthetic methods illustrated in Schemes 1-11. Those of skill in the art will appreciate that a preferred synthetic route to the compounds of the invention will consist of attaching or incorporating soft-moieties to cycloalkylmethylamines of Formulae (I), (II), (III) and (IV). Several methods have been described in the art for the synthesis of cycloalkylmethylamine analogs (see, e.g. Mattson, R. J. et al. U.S. Pat. No. 5,596,019; Lulla, A. et al., International Application Publication No. WO 2004/096202; Senanayake, C. H. et al., International Application Publication No. WO 02/083631; Vyas, S. K. et al., International Application Publication No. WO 02/36540; Jerussi, T. P. et al., International Application Publication No. WO 02/060424; Jeffery, J. E. et al., *J. Chem. Soc. Perkin Trans* 1, 1996, 2583-2589.). Other methods are known in the art for synthesizing cycloalkylmethylamines, which are readily accessible to the skilled artisan. The soft-moieties attached to spacers thereof are commercially available or can be prepared by established procedures (See e.g., Green et al., "Protective Groups in Organic Chemistry," (Wiley, 3rd ed., 1999); Harrison et al "Compendium of Synthetic Organic Methods," vols. 1-8 (John Wiley and Sons, 1971-1996); "Beilstein Handbook of Organic Chemistry, Frankfurt, Germany; Feiser et al, "Reagents for Organic Synthesis," Volumes 1-45, Karger, 1991; March, Advanced Organic Chemistry," Wiley Interscience, 4th ed., 1991; Larock "Comprehensive Organic Transformations," Wiley-VCH Publishers, 2nd ed., 1999; Paquette, "Encyclopedia of Reagents for Organic Synthesis," John Wiley and Sons, 1st ed., 1995).

Accordingly, starting materials useful for preparing compounds of the invention and intermediates thereof are commercially available or can be prepared by well-known synthetic methods. Other methods for the synthesis of cycloalkylmethylamines described herein are either described in the art or will be readily apparent to the skilled artisan in view of the references provided above and may be used to synthesize the compounds of the invention. Accordingly, the methods presented in the Schemes herein are illustrative rather than comprehensive.

In one general method for synthesis of compounds of Formulae (I)-(IV) is described in Scheme 1. An appropriate substituted phenylacetonitrile (1) is reacted with dibromoalkane (2) in appropriate solvent (e.g., ether, THF, dioxane, DMF, DMSO) at a temperature between 10 and 100° C., preferably between 20 and 75° C. in the presence of a base (e.g., NaH, KOH) to give cycloalkylnitrile (3). The cycloalkylnitrile compounds are used to synthesize compounds (6) using a tandem Grignard-reduction method. The typical procedure involves the reaction of compound (3) with an appropriate Grignard reagent ($R^{11}MgBr$) in presence of an appropriate solvent (e.g., ether, THF, toluene) at a temperature between 0 and 90° C. for 1 to 24 hours. Then the resulting adduct is subjected to reduction without any workup procedures using reducing agent like sodium borohydride according to a standard or an established procedure (see, Jeffery et al., J. Chem. Soc., Perkin Trans. 1, 1996, 2583-2589) to produce the corresponding cycloalkylmethylamine (6). The amino group in compounds 6 can be alkylated directly using appropriate alkyl halides or sequentially by reductive alkylation methods using standard procedures well known in the art to provide compounds (10). In one method, an appropriate carboxylic acid can be coupled to a compound (6) using standard peptide coupling reagents like DCC or DIC followed by reducing the corresponding amide (9) with using a reducing agent like borane under standard reduction conditions well known in the art. Compound (10) can be further alkylated using appropriate alkyl halides in the presence of a suitable base (e.g., TEA, DIEA, pyridine, cesium carbonate) under standard conditions.

In another general method for synthesis of compounds of Formulae (I)-(IV) can be prepared from cycloalkylmethylamines (6) as described in Scheme 2. Compound (6) may be reacted with an appropriate spacer carrying a soft-moiety (13) under standard alkylating conditions well known in the art to provide the corresponding cycloalkylmethylamine (14).

Scheme 1

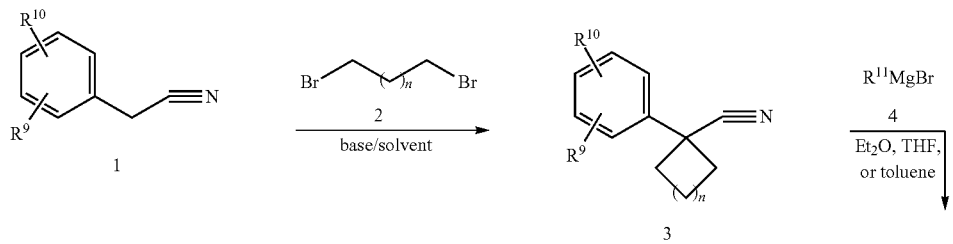

-continued

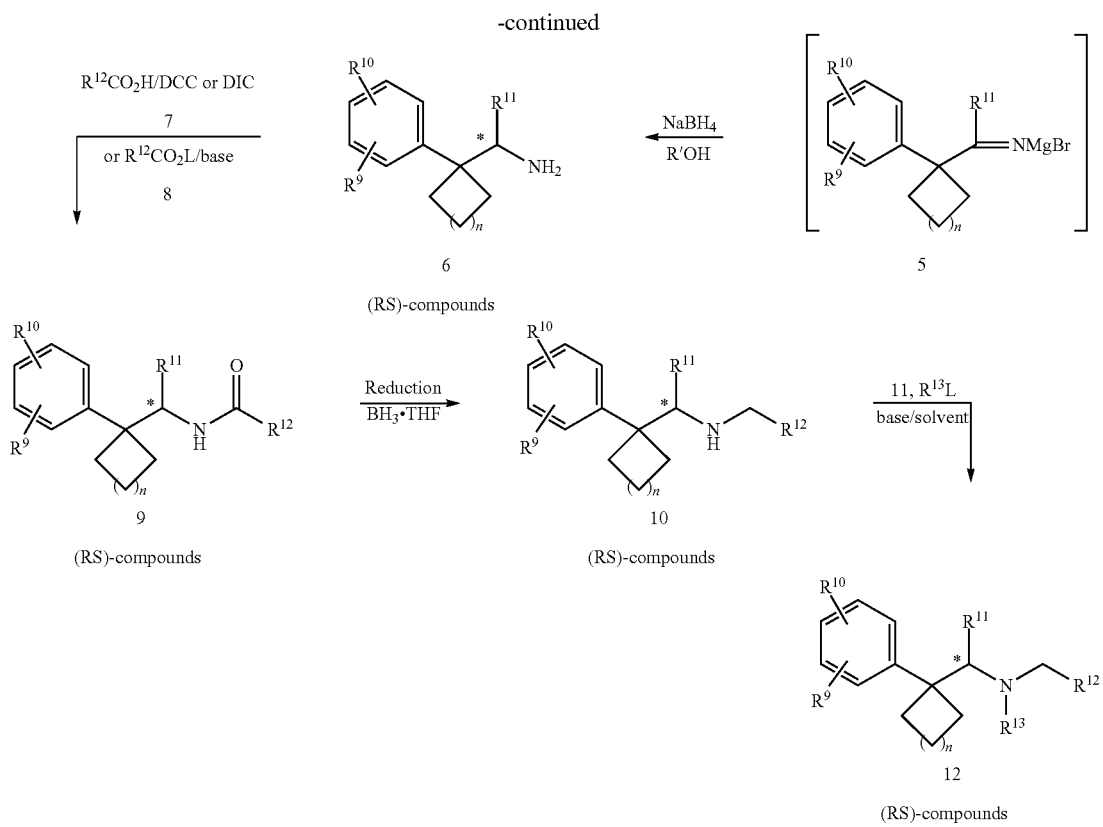

R'OH = Methanol, ethanol, isopropanol
L = Cl, Br, I
n = 0, 1, 2, 3, 4, or 5

Scheme 2

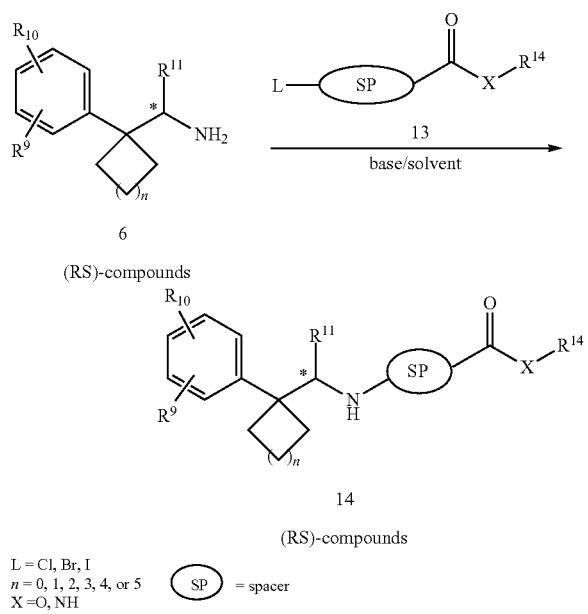

L = Cl, Br, I
n = 0, 1, 2, 3, 4, or 5
X = O, NH

SP = spacer

Another general method for synthesis of compounds of Formulae (I)-(IV) begins with an appropriate cycloalkylnitrile (3) in a stepwise fashion as illustrated in Scheme 3. Here reaction of compound (3) with an appropriate Grignard reagent (15) carrying a masked functional group like protected hydroxyl moiety followed by in situ reduction of the corresponding imine (16) using sodium borohydride as described above for the synthesis of compound (6) in Scheme 1 affords the corresponding cycloalkylmethylamine (17). A number of Grignard reagents having masked functional or pro-functional groups can be used in this reaction and most preferred functional groups is hydroxy (OH). Several Grignard reagents carrying masked functional group are commercially available and they can also be prepared by methods well known to the skilled artisan. Then, protection of amino moiety with a global protecting group, benzyloxycarbonyl group by treating with a commercially available reagent benzylchloroformate followed by deprotection of tert-butyldimethylsilane (TBS) protecting group under standard conditions affords the corresponding N-benzyloxycarbonyl (N-Cbz) protected cycloalkylmethylamine (18). Compound (18) upon subjected to oxidation using pyridinium chlorochromate (PCC) or any other standard oxidizing agents to provide carboxylic acid which after reacting with an appropriate alcohol ($R^{14}OH$) or amine ($R^{14}NH_2$) affords the corresponding carboxylic acid ester or amide derivative of N-Cbz protected cycloalkylmethylamine (22). Deprotection of Cbz protecting group with palladium on activated carbon in hydrogen atmosphere affords compound (23). The amino moiety of cycloalkylmethylamine (23) can be further derivatized using alkyl halides ($R^{13}L$) under standard reaction conditions well known in the art of as described for the compounds (12) and (14) in Scheme 1 and 2, respectively.

Another general method for synthesis of compounds of Formulae (I)-(IV) begins with an appropriate cycloalkylnitrile (3) in a stepwise fashion as illustrated in Scheme 4. Here reaction of compound (3) with an appropriate Grignard reagent (25) carrying a masked aldehyde group followed by in situ reduction of the corresponding imine (26) using sodium borohydride as described above for the synthesis of compounds (6) and (17) in Scheme 1 and 3, respectively, affords the corresponding cycloalkylmethylamine (27). A number of Grignard reagents having masked aldehyde functional group can be used in this reaction and most preferred ones are 5- and 6-member cyclic acetals. Several Grignard reagents carrying masked functional group are commercially available and they can also be prepared by methods well known to the skilled artisan. Then, protection of amino moiety in with a global protecting group, benzyloxycarbonyl group by treating with a commercially available reagent benzylchloroformate followed by acid catalyzed cleavage of cyclic acetal protecting group under standard conditions affords the corresponding N-Cbz protected cycloalkylmethylamine (29). Compound (29) upon subjected to oxidation using pyridinium chlorochromate (PCC) or any other standard oxidizing agents to provide carboxylic acid which after reacting with an appropriate alcohol ($R^{14}OH$) or amine ($R^{14}NH_2$) affords the corresponding carboxylic acid ester or amide derivative of N-Cbz protected cycloalkylmethylamine (30) which can be further converted in to compounds 23 and 24 as illustrated in Scheme 3.

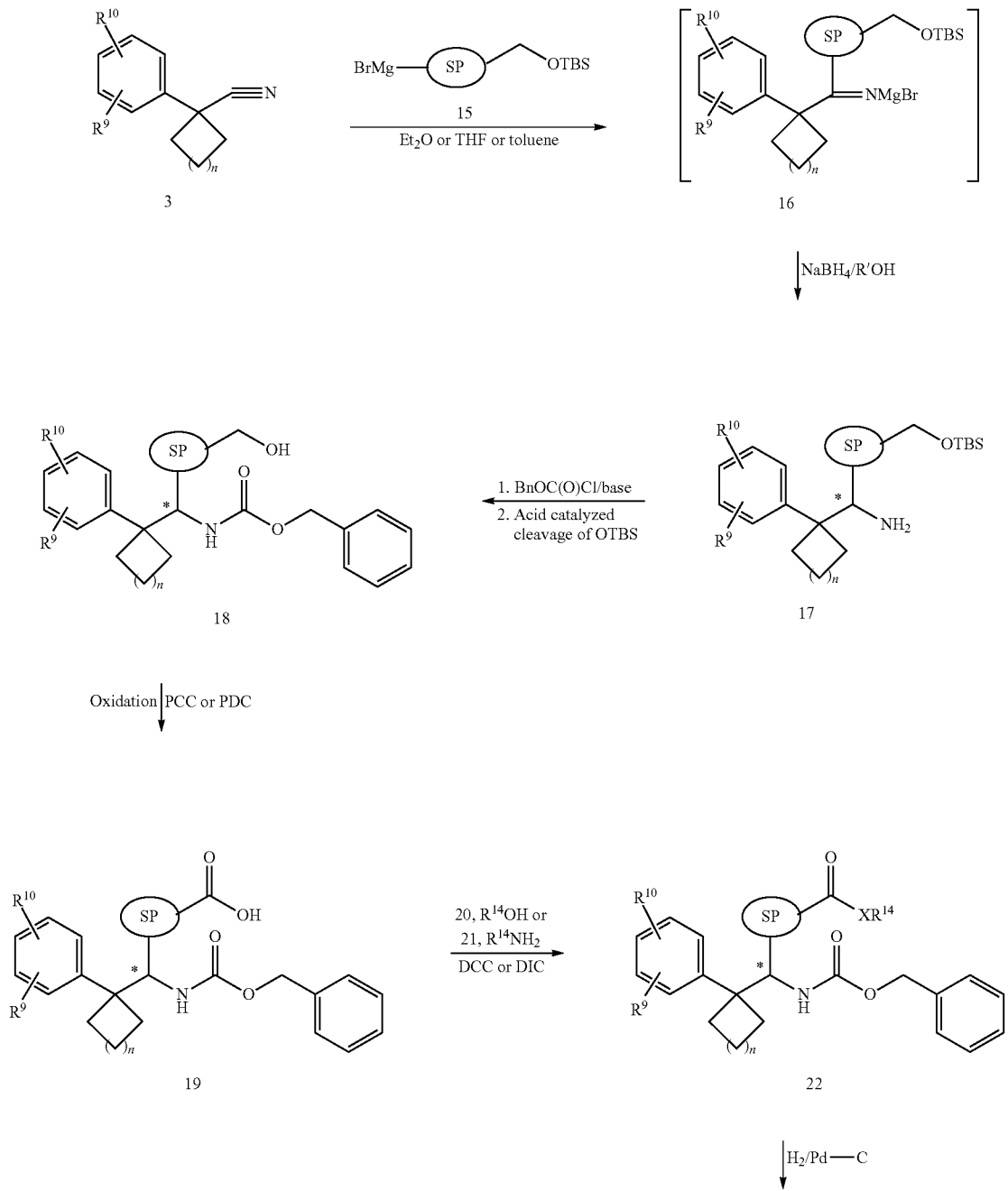

23
24
-continued
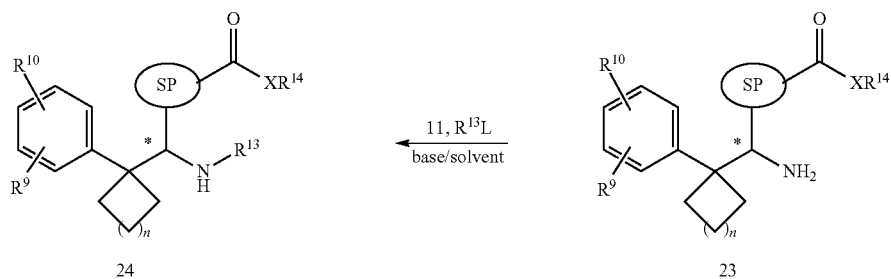
R'OH = Methanol, ethanol, isopropanol
L = Cl, br, I
$n$ = 0, 1, 2, 3, 4, or 5
X = O, NH
SP = spacer
Scheme 4
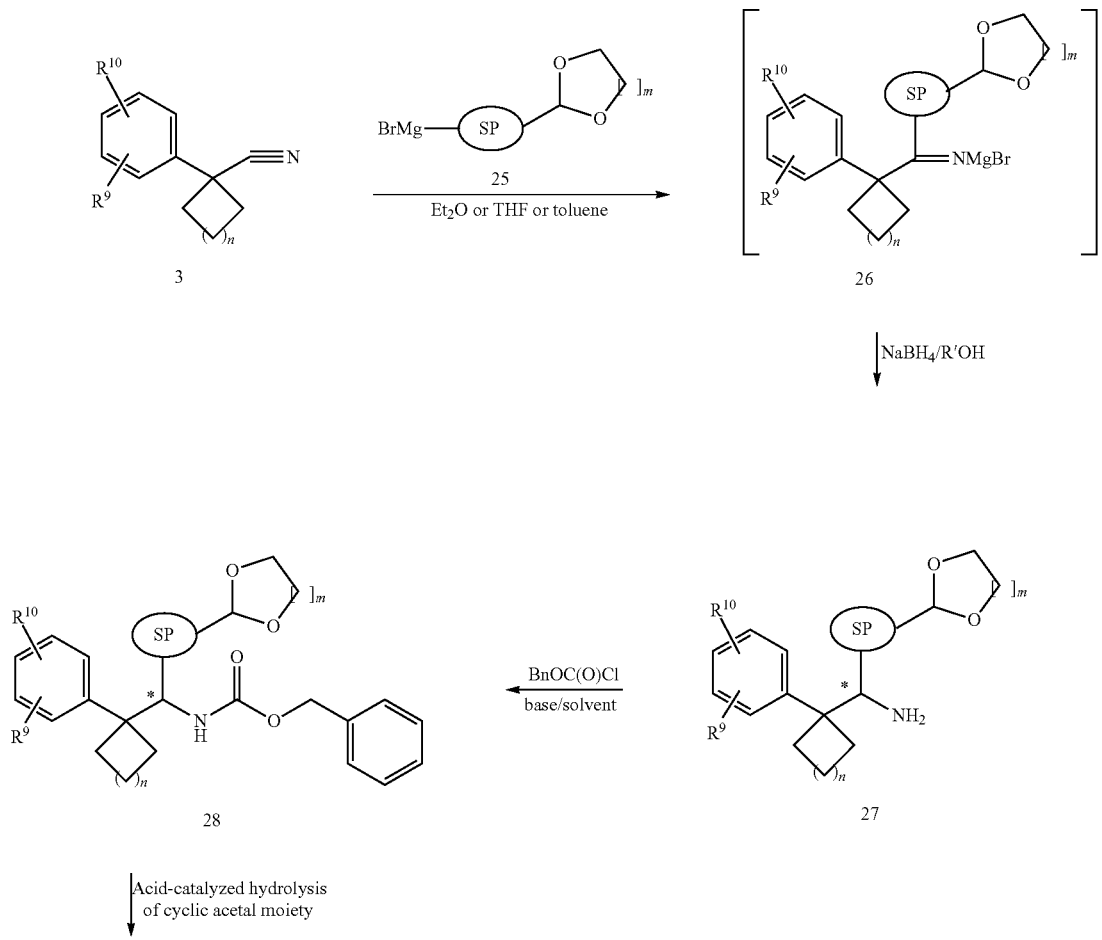

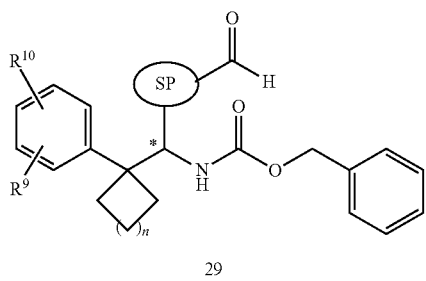

29

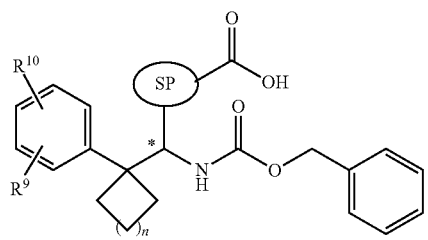

30 → as described in Scheme 3 → 22, 23, and 24

R'OH = Methanol, ethanol, isopropanol
m = 1, 2
n = 0, 1, 2, 3, 4, or 5

SP = spacer

Another general method for synthesis of compounds of Formulae (I)-(IV) is described in Scheme 5, where cycloalkylmethylamines carrying appropriate substituents having esterase cleavable group such as carboxylic acid esters and amides are synthesized. In a typical example, a reaction of phenylacetonitrile (3) and appropriate halide (31) carrying protected hydroxyl group in the presence of a base (e.g., potassium carbonate, cesium carbonate) in a solvent (e.g., acetone, DMF) at a temperature between ambient and 125° C., preferably between 25° C. and 95° C. provides the expected compound (32). The cycloalkylmethylamines (37) carrying a soft-moiety can be prepared from compound (32) in a stepwise fashion as illustrated in Scheme 4 and also by using the methods described in Schemes 1 to 3.

Scheme 5

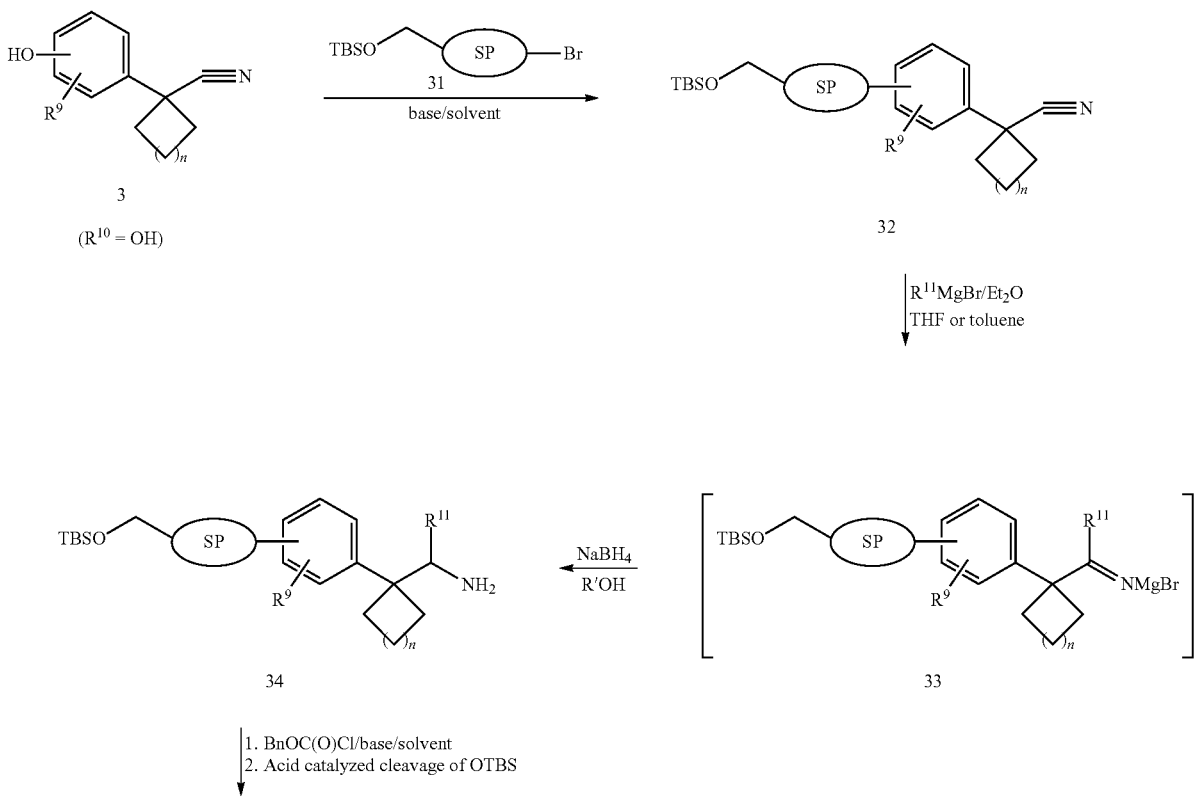

-continued
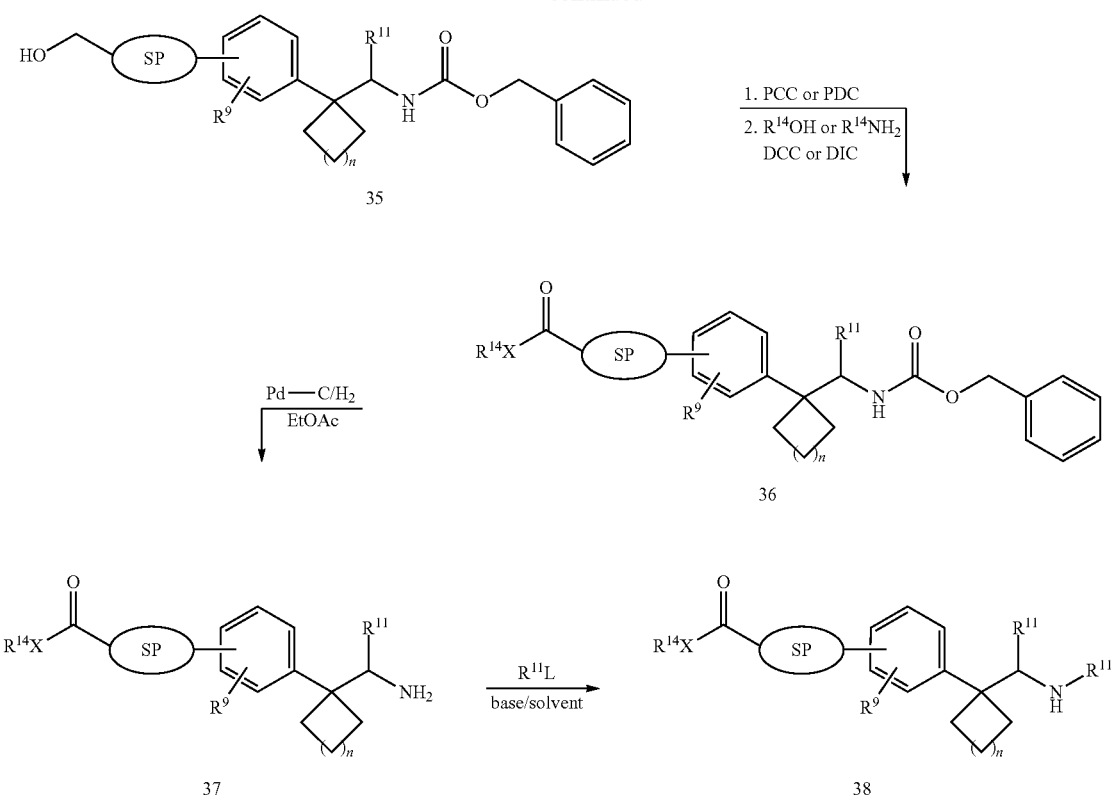
R'OH = Methanol, ethanol, isopropanol
L = Cl, Br, I
n = 0, 1, 2, 3, 4, or 5
X = O, NH
SP = spacer
Scheme 6
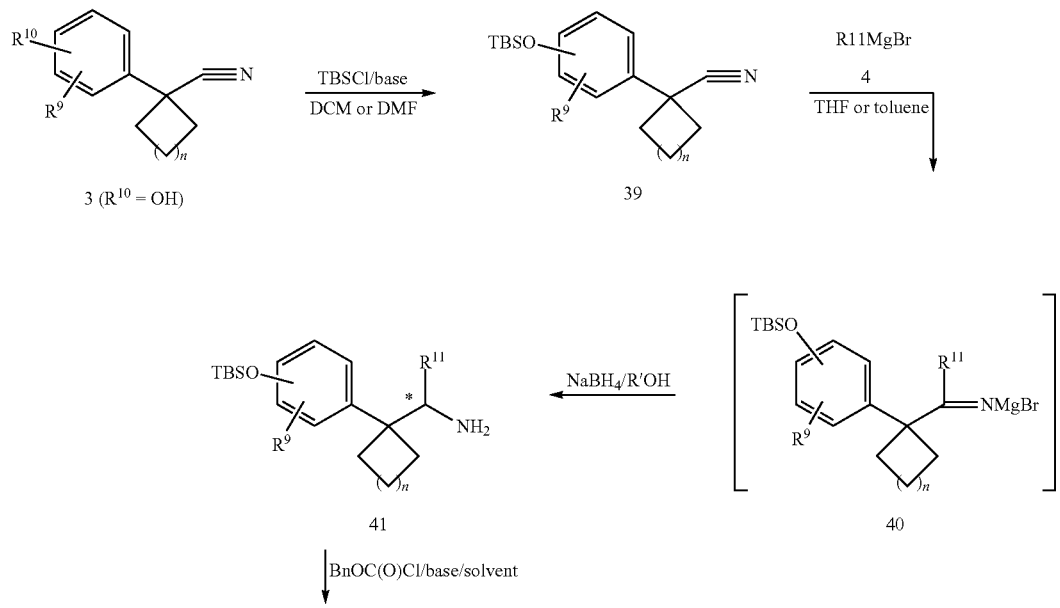

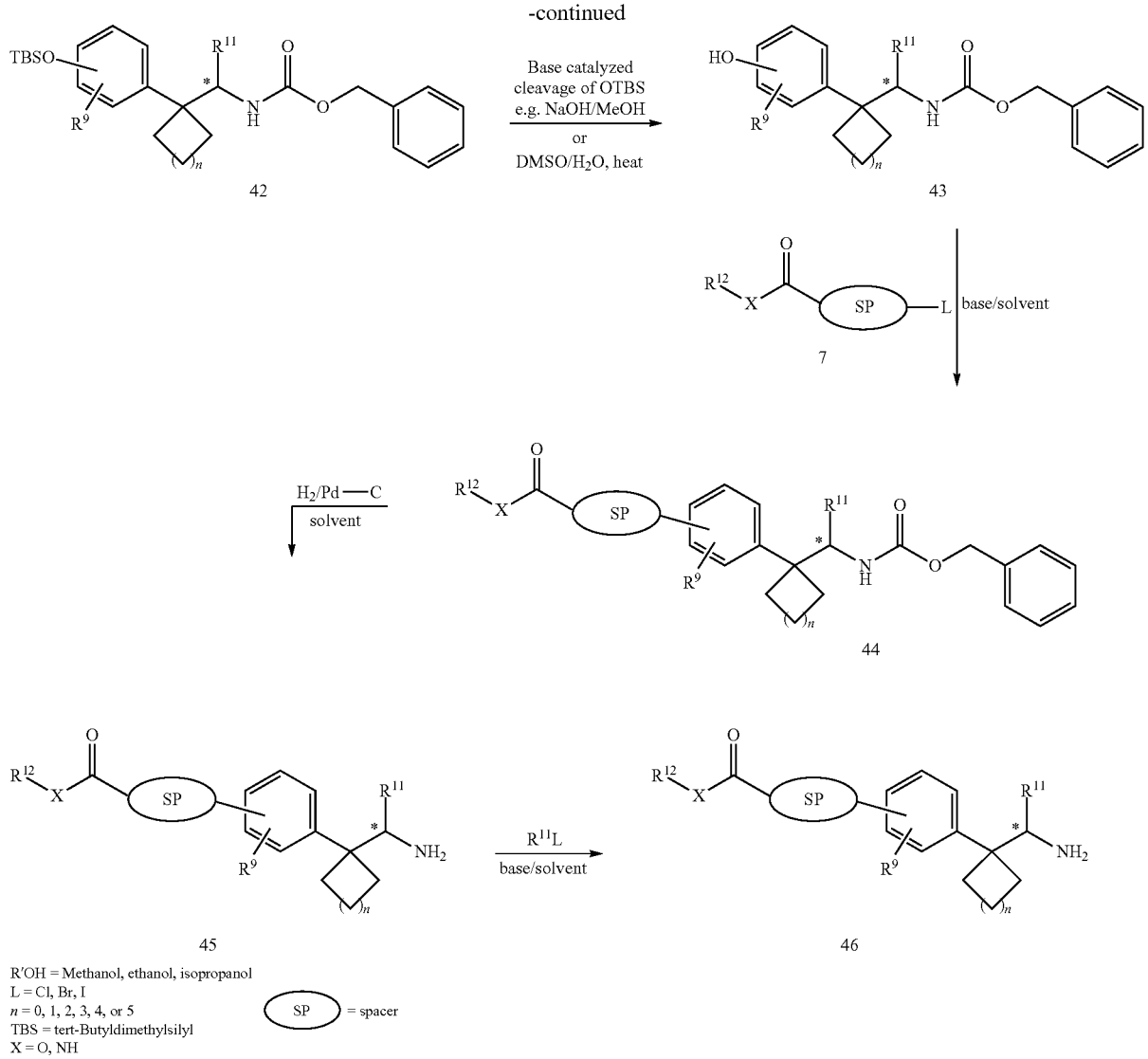

Another general method for synthesis of compounds of Formulae (I)-(IV) is described in Scheme 6, where cycloalkylmethylamines carrying appropriate substituents having terminal ester or amide groups are synthesized. In a typical example, a reaction of phenylacetonitrile (3, $R^{10}$=OH) carrying a phenolic OH moiety is protected with an appropriate protecting group like tert-butyldimethylsilyl (TBS) group under standard reaction conditions to give the compound 39. The compound 39 is reacted with appropriate Grignard reagent 4 ($R^{11}$ MgBr) as described for the synthesis of compound 6 in Scheme 1 to afford compound 41. The cycloalkylmethylamines (45) and (46) carrying a soft-moiety can be prepared from compound (41) in a stepwise fashion as illustrated in Scheme 5 and also by using the methods described in Schemes 1 to 4.

Scheme 7

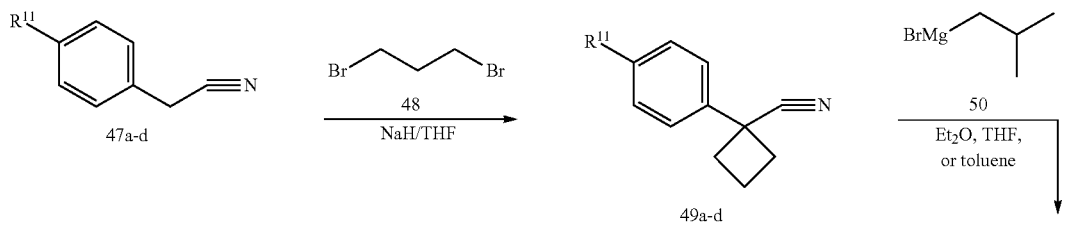

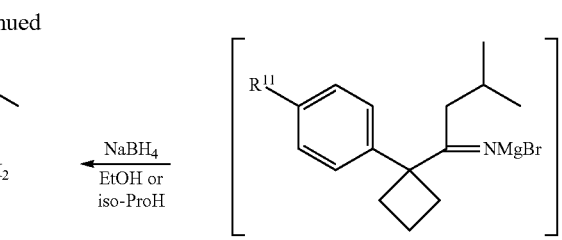
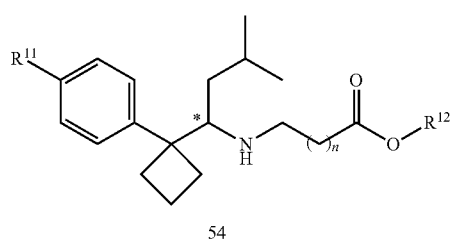
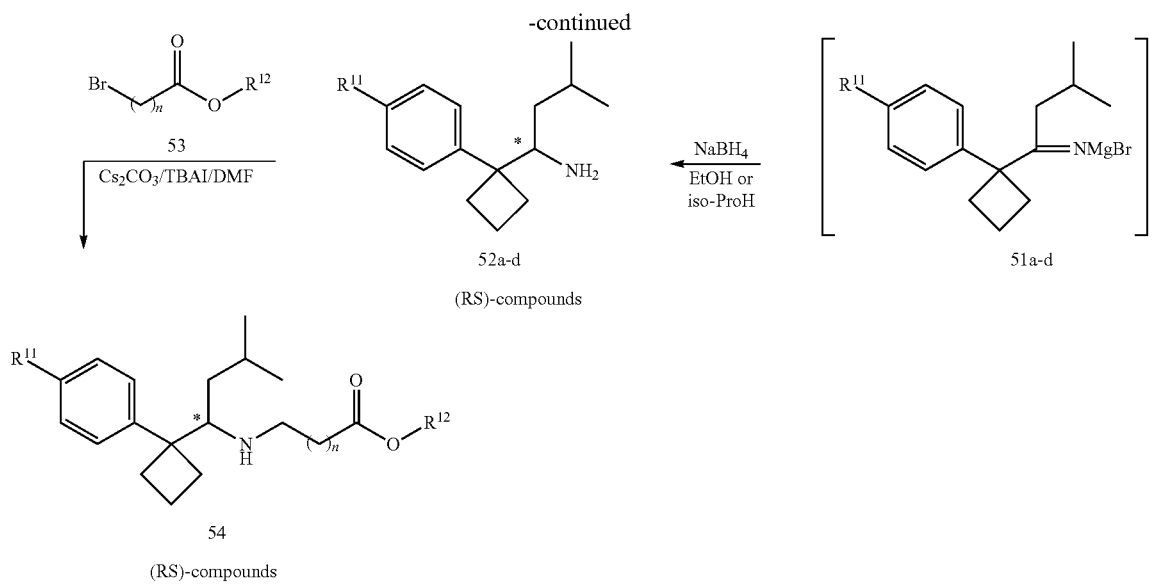

Examples:

47-52a: $R^{11}$ = Cl
 b: $R^{11}$ = benzyloxy
 c: $R^{11}$ = 4-methoxybenzyloxy
 d: $R^{11}$ = tert-butyldimethylsilyloxy 54a: $n$ = 0; $R^{11}$ = Cl; $R^{12}$ = ethyl
 b: $n$ = 2, $R^{11}$ = Cl; $R^{12}$ = ethyl
 c: $n$ = 2, $R^{11}$ = Cl; $R^{12}$ = isopropyl
 d: $n$ = 2, $R^{11}$ = Cl; $R^{12}$ = isobutyl
 e: $n$ = 2, $R^{10}$ = Cl; $R^{12}$ = benzyl
 f: $n$ = 3, $R^{11}$ = Cl; $R^{12}$ = ethyl In one method selected cyclobutanealkylamines comprising Formula (IV) were prepared as described in Scheme 7. An appropriate substituted phenylacetonitrile (47) was reacted with 1,3-dibromopropane (48) in anhydrous tetrahydrofuran at ice-bath temperature to room temperature to give the corresponding cycloalkylnitrile (49). The cycloalkylnitrile compounds (49) were used for synthesizing compounds (52) using a tandem Grignard-reduction method as described in the general method for synthesis of cycloalkylmethylamines and illustrated in Scheme 1. The amino group in compounds 52 was alkylated directly using appropriate alkyl halides carrying a terminal ester moiety using cesium carbonate in a polar aprotic solvent DMF at room temperature to 60° C. to afford the corresponding N-alkylated compounds 54. The presence of tetrabutylammonium iodide in the reaction mixture was found to increase the yield of 54 and also accelerate the completion of the reaction to a great extent.

Scheme 8

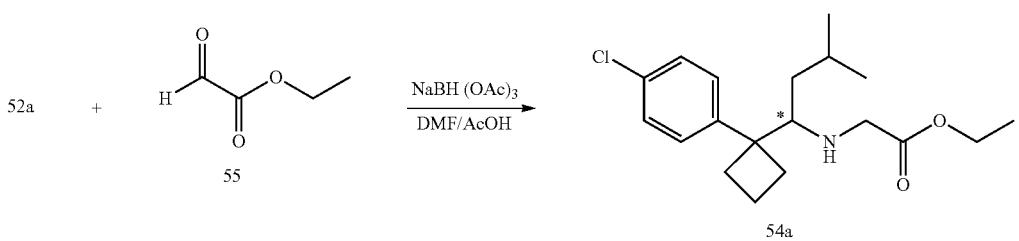

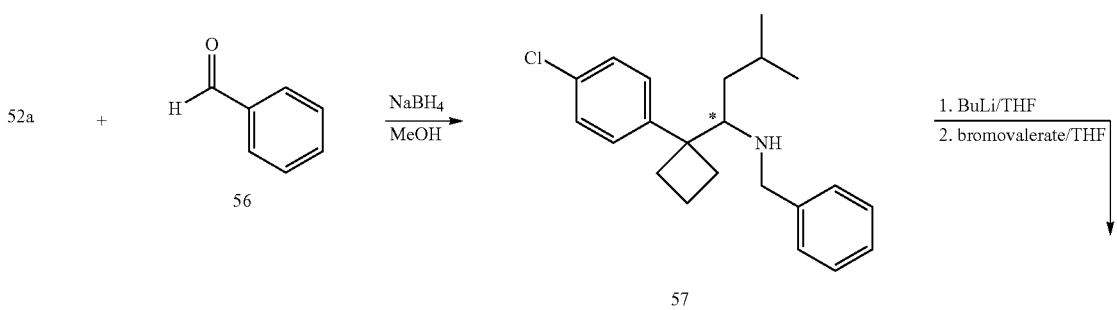

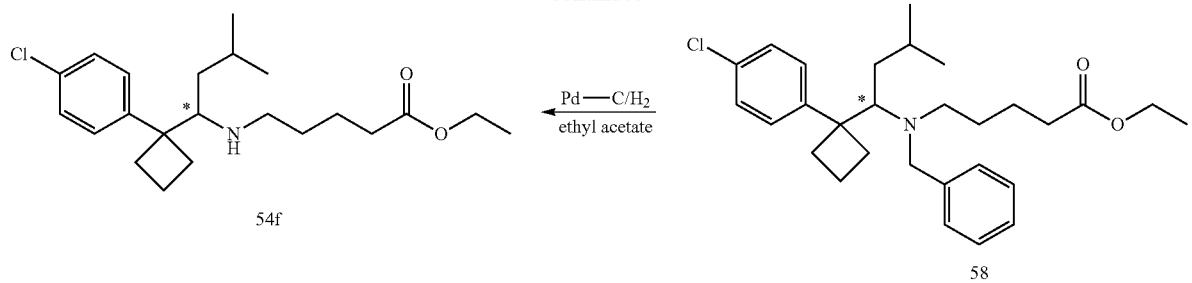

Other methods for synthesis of cycloalkylamines comprising Formula (I) and (IV) were prepared as described in Scheme 8. The cycloalkylamine carrying a terminal carboxylic acid ester moiety 54a was prepared by reacting ethyl glyoxylate under reductive alkylation conditions using sodium triacetoxyborohydride as reducing agent. The cycloalkylamine carrying a terminal carboxylic ester moiety 54e was prepared from the cycloalkylamine 52a in three steps as described in Scheme 8. The compound 57 was prepared by reductive alkylation of 52a with benzaldehyde under standard conditions in good yield which was further alkylated with 5-bromovalerate using a strong base n-butyllithium to give the corresponding trialkyl compound 58. The benzyl group in compound 58 was cleaved off under standard hydrogenolysis conditions using palladium on activated carbon in presence of hydrogen atmosphere and few drops of hydrochloric acid in ethyl acetate as solvent to give the corresponding amine 54e.

The synthesis of building blocks 47 is illustrated in Scheme 9. 4-Chlorophenylacetonitrile (47a) is commercially available and was purchased from Aldrich. The compounds 47b-d were prepared from 4-hydroxyphenylacetonitrile (59). The compound 47b was prepared by alkylating 59 with benzyl bromide using potassium carbonate as base in DMF as solvent in good yield. Similarly, the compound 47c was synthesized alkylating 59 with 4-methoxybenzaldehyde in good yield. The reaction of tert-butyldimethylsilyl chloride (TBSCl) with 59 in presence of base imidazole and 10 mol % of N,N-dimethylaminopyridine (DMAP) in dichloromethane afforded the corresponding 47d in good yield.

Scheme 9

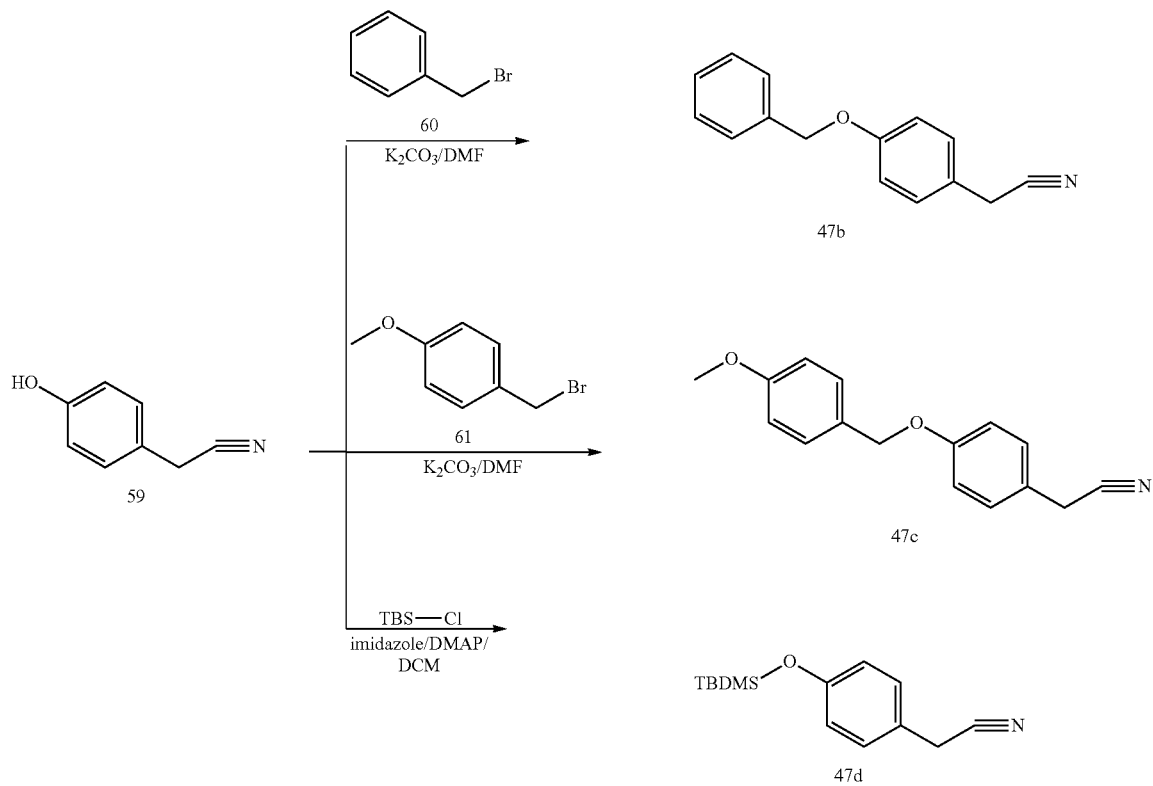

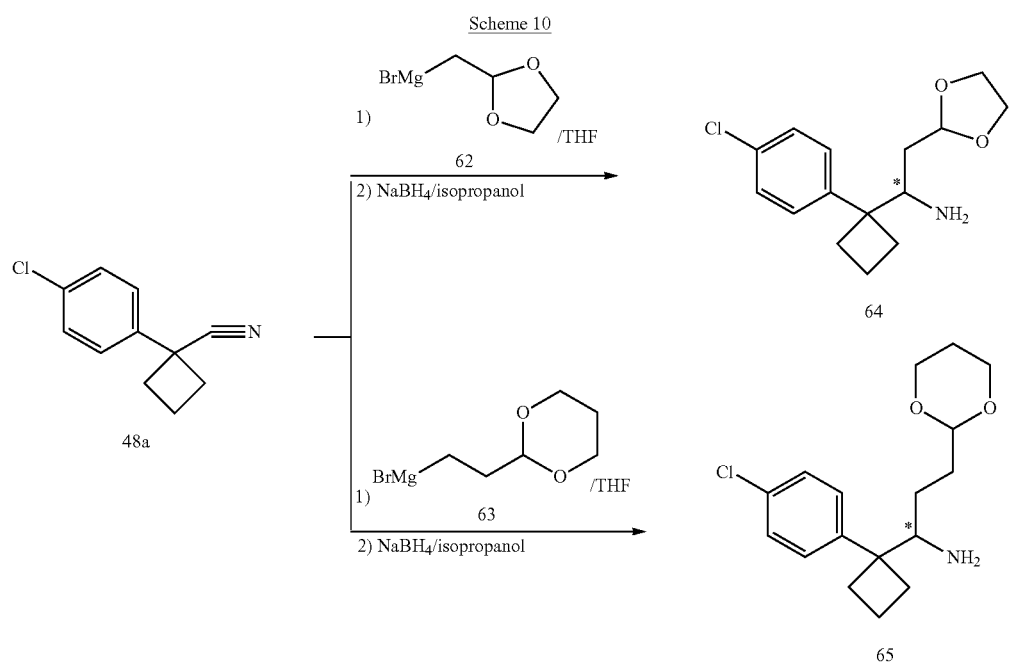

In another method cyclobutanealkylamines comprising Formula (I) and (IV) were prepared as described in Scheme 10. 4-Chlorophenylcyclobutaneacetonitrile (48a) was reacted with commercially available Grignard reagents having masked aldehyde functional group 62 and 63 as illustrated in Scheme 4 give the corresponding cyclobutanealkylamines carrying masked aldehyde functional group 64 and 65, respectively. The compounds 64 and 65 can be further derivatized to give cyclobutanealkylamines carrying esters and amides as illustrated in Scheme 4.

In another method selected examples of cycloalkylamines carrying terminal esters or amides comprising general Formulae (I) and (II) were prepared as described in Scheme 11. The amine moiety in cyclobutanealkylamine 52d was protected with tert-butyloxycarbonyl (BOC) group to give N—BOC protected amine 66. Then, the TBS protecting group on 66 was cleaved off under neutral conditions using aqueous DMSO at 50-90° C. to give 67. The N—BOC protected phenol 67 was alkylated with ethyl bromoacetate under standard alkylating conditions using cesium carbonate as base in anhydrous DMF to afford the compound 69 which after treatment with trifluoroacetic acid in DCM gave the corresponding cyclobutanealkylamine carrying terminal carboxylic acid ester substituents 70.

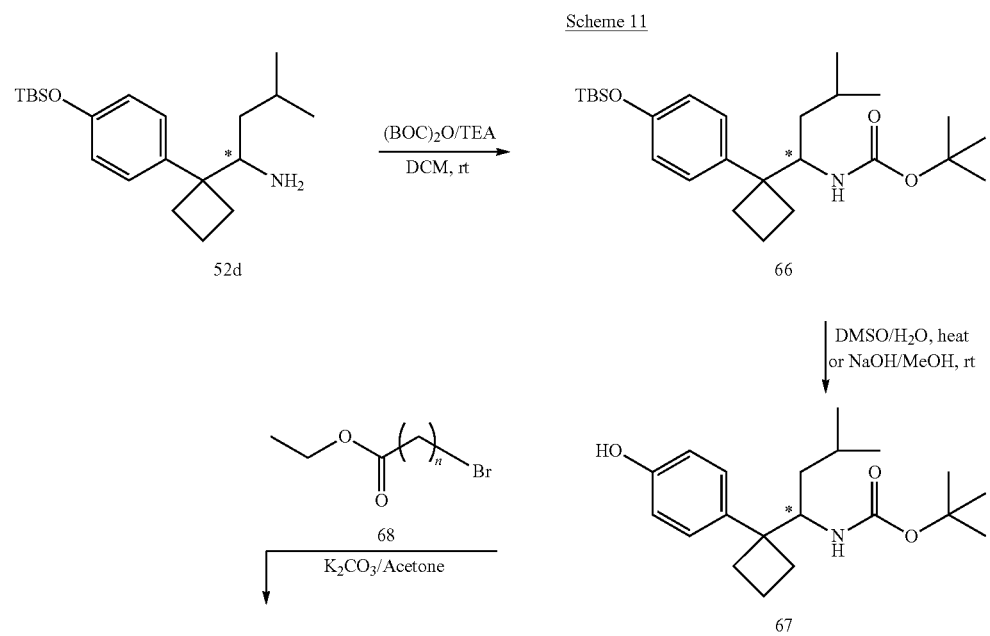

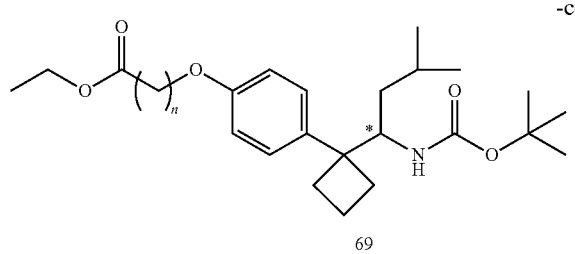

69

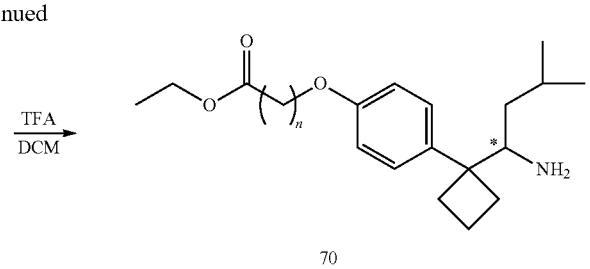

70

68-70a: $n = 1$
b: $n = 2$

4.4 Therapeutic Uses of Compounds of Structural Formulae

The present invention provides methods of treating and preventing obesity and associated co-morbid conditions. The term "co-morbid conditions associated with obesity" used in this document means medical conditions known to those skilled in the art to be associated with obesity. The term includes but not limited to the following: diabetes including non-insulin dependent diabetes mellitious, impaired glucose tolerance, hypertension, coronary thrombosis, stroke, depression, anxiety, psychoses (for example schizophrenia), tardive dyskinesia, drug addiction, drug abuse, cognitive disorders, Alzheimer's disease, cerebral ischaemia, obsessive-compulsive behavior, panic attacks, social phobias, eating disorders such as bulimia, anorexia, snacking and binge eating, lipid syndromes, hyperglycemia, hyperlipidemia, and stress in mammals particularly humans.

In addition, the compounds, compositions, and methods of the present invention can be used in the treatment or prevention of metabolic diseases and conditions arising therefrom, or for example non exercise activity thermogenesis and increased metabolic rate, sexual dysfunction, sleep apnoea, premenstrual syndrome, urinary incontinence including stress incontinence, hyperactivity disorders, hiatial hernia, and reflux esophagitis, pain, especially neuropathic pain, weight gain associated with drug treatment, chronic fatigue syndrome, osteoarthritis and gout, cancers associated with weight gain, menstrual dysfunction, gallstones, orthostatic hypotension and pulmonary hypertension.

The compounds, compositions, and methods of the present invention can be useful in preventing cardiovascular disease, and in reducing platelet adhesiveness, in aiding weight loss after pregnancy, reducing the craving to smoke and in aiding weight loss after smoking cessation. The present invention can also be useful in lowering uric acid levels and lipid levels in mammals particularly humans.

In accordance with the invention, a compound and/or a composition containing a compound of structural Formulae (I), (II), (III) or (IV) is administered to a patient, preferably a human, suffering from obesity and associated with co-morbid diseases and/or disorders Further, in certain embodiments, the compounds and/or compositions of the invention are administered to a patient, preferably a human, as a preventive measure against various diseases or disorders. Thus, the compounds and/or compositions containing compound(s) of structural Formulae (I), (II), (III) or (IV) may be administered as a preventive measure to a patient having a predisposition for obesity and associated co-morbid diseases and/or disorders (see, Montana, J. G. International Application Publication No. WO 2004/058237; Lulla, A. et al., International Application Publication No. WO 2004/096202; Jerussi, T. P. et al., International Application Publication No. WO 02/060424; Senanayake, C. H. et al., International Application Publication No. WO 01/51453; Heal, D. J. International Application Publication No. WO 01/00205; Birch, A. M. et al., International Application Publication No. WO 01/00187; Mueller, P. International Application Publication No. WO 00/32178; Bailey, C. International Application Publication No. WO 98/11884; Kelly, P. International Application Publication No. WO 98/13034).

Thus, those of skill in the art may readily assay and use the compounds and/or compositions containing compound(s) of structural Formulae (I), (II), (III) or (IV) to treat obesity and associated co-morbid diseases and/or disorders.

4.5. Therapeutic/Prophylactic Administration

The compounds, and/or compositions containing compounds(s), of structural Formulae (I), (II), (III) or (IV) can be advantageously used in human medicine. As previously described in Section 4.4 above, compounds and compositions containing compound(s) of structural Formulae (I), (II), (III) or (IV) are useful for the treatment or prevention of obesity and associated co-morbid diseases and/or disorders.

When used to treat or prevent the above disease or disorders compounds and/or compositions of the invention can be administered or applied singly, in combination with other agents. The compounds and/or compositions of the invention can also be administered or applied singly, in combination with other pharmaceutically active agents, including other compounds and/or compositions of the invention.

The current invention provides methods of treatment and prophylaxis by administration to a patient of a therapeutically effective amount of a composition and/or compound of the invention. The patient may be an animal, is more preferably a mammal, and most preferably a human.

The present compounds and/or compositions of the invention, which comprise one or more compounds and/or compositions of the invention are preferably administered orally. The compounds and/or compositions of the invention may also be administered by any other convenient route, for example, by infusion or bolus injection, by absorption through epithelial or mucocutaneous linings (e.g., oral mucosa, rectal and intestinal mucosa, etc.). Administration can be systemic or local. Various delivery systems are known, (e.g., encapsulation in liposomes, microparticles, microcapsules, capsules, etc.) that can be used to administer a compound and/or composition of the invention. Methods of administration include, but are not limited to, intradermal, intramuscular, intraperitoneal, intravenous, subcutaneous, intranasal, epidural, oral, sublingual, intranasal, intracerebral, intravabinal, transdermal, rectally, by inhalation, or topically, particularly to the ears, nose, eyes or skin.

In particularly, preferred embodiments, the compounds and/or compositions of the invention can be delivered via sustained release systems, preferably oral sustained release systems. In one embodiment, a pump may be used (see, Langer, supra; Sefton, 1987, CRC Crit. Ref Biomed. Eng. 14:201; Saudek et al., 1989, N. Engl. J. Med. 321:574).

In another embodiment, polymeric materials can be used (see "Medical Applications of Controlled Release," Langer and Wise (eds.), Wiley, New York (1984); Ranger and Peppas, 1983, J. Macromol. Sci. Rev. Macromol Chem. 23:61; see also Levy et al., 1985, Science 228:190; During et al., 1989, Ann. Neurol. 25:351; Howard et al, 1989, J. Neurosurg. 71:105). In a preferred embodiment, polymeric materials are used for oral sustained release delivery. Preferred polymers include sodium carboxymethylcellulose, hydroxypropylcellulose, hydroxypropylmethylcellulose and hydroxyethylcellulose (most preferred, hydroxypropylmethylcellulose). Other preferred cellulose ethershave been described in the art (Bamba et al., Int. J. Pharm., 1979, 2, 307).

In another embodiment, enteric-coated preparations can be used for oral sustained release administration. Preferred coating materials include polymers with a pH-dependent solubility (i.e., pH-controlled release), polymers with a slow or pH-dependent rate of swelling, dissolution or erosion (i.e., time controlled release), polymers that are degraded by enzymes (i.e., enzyme controlled release) and polymers that form firm layers that are destroyed by an increase in pressure (i.e., pressure-controlled release).

In still another embodiment, osmotic delivery systems are used for oral sustained release administration (Verma et al., Drug Dev. Ind. Pharm., 2000, 26:695-708). In a preferred embodiment, OROS® osmotic delivery systems sold by Alza Corporation of Mountain View, Calif. are used for oral sustained release delivery devices (See for example, Theeuwes et al., U.S. Pat. No. 3,845,770; and Theeuwes et al, U.S. Pat. No. 3,916,899).

In yet another embodiment, a controlled-release system can be placed in proximity of the target of the compounds and/or composition of the invention, thus requiring only a fraction of the systemic dose (See, e.g., Goodson, in "Medical Applications of Controlled Release," supra, vol. 2, pp. 115-138 (1984)). Other controlled-release systems discussed in Langer, 1990, Science 249:1527-1533 may also be used.

The compounds, and/or compositions containing compound(s) of structural Formulae (I), (II), (III) or (IV) of the invention may be cleaved either chemically and/or enzymatically. One or more enzymes present in the stomach, intestinal lumen, intestinal tissue, blood, liver, brain or any other suitable tissue of a mammal may enzymatically cleave the compounds and/or compositions of the invention.

4.6 Compositions of the Invention

The present composition contain a therapeutically effective amount of one or more compounds of the invention, preferably in purified form, together with a suitable amount of a pharmaceutically acceptable vehicle, which so as to provide the form for proper administration to a patient. When administered to a patient, the compounds of the invention and pharmaceutically acceptable vehicles are preferably sterile. Water is preferred vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present agents, or pH buffering agents. In addition, auxiliary, stabilizing, thickening, lubricating and coloring agents may be used.

Pharmaceutical compositions comprising a compound of the invention may be manufactured by means of conventional mixing, dissolving, granulating, dragee-making levigating, and emulsifying, encapsulating, entrapping or lyophilizing process. Pharmaceutical compositions may be formulated in conventional manner using one or more physiologically acceptable carriers, diluents, excipients or auxiliaries, which facilitate processing of compounds of the invention into preparations which can be used pharmaceutically. Proper formulation is dependent upon the route of administration chosen.

The present compositions can take the form of solutions, suspensions, emulsion, tablets, pills, pellets, and capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., Grosswald et al., U.S. Pat. No. 5,698,155). Other examples of suitable pharmaceutical vehicles have been described in the art (see Remington's Pharmaceutical Sciences, Philadelphia College of Pharmacy and Science, 17$^{th}$ Edition, 1985). Preferred compositions of the invention are formulated for oral delivery, particularly for oral sustained release administration.

Compositions for oral delivery may be in the form of tablets, lozenges, aqueous or oily suspensions, granules, powders, emulsions, capsules, syrups or elixirs, for example. Orally administered compositions may contain one or more optionally agents, for example, sweetening agents such as fructose, aspartame or saccharin; flavoring agents such as peppermint, oil of wintergreen, or cherry coloring agents and preserving agents to provide a pharmaceutically palatable preparation. Moreover, where in tablet or pill form, the compositions may be coated to delay disintegration and absorption in the gastrointestinal tract, thereby providing a sustained action over an extended period of time. Selectively permeable membranes surrounding an osmotically active driving compound are also suitable for orally administered compounds of the invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about mM to about 50 mM) etc. Additionally, flavoring agents, preservatives, coloring agents, bile salts, acylcamitines and the like may be added.

Compositions for administration via other routes may also be contemplated. For buccal administration, the compositions may take the form of tablets, lozenzes, etc. formulated in conventional manner. Liquid drug formulations suitable for use with nebulizers and liquid spray devices and EHD aerosol devices will typically include a compound of the invention with a pharmaceutically acceptable vehicle. Preferably, the pharmaceutically acceptable vehicle is a liquid such as alcohol, water, polyethylene glycol or a perfluorocarbon. Optionally, another material may be added to alter the aerosol properties of the solution or suspension of compounds of the invention. Preferably, this material is liquid such as alcohol, glycol, polyglycol or fatty acid. Other methods of formulating liquid drug solutions or suspension suitable for use in aerosol devices are known to those of skill in the art (see, e.g., Biesalski, U.S. Pat. No. 5,112,598; Biesalski, U.S. Pat. No. 5,556,611). A compound of the invention may also be formulated in rectal or vaginal compositions such as suppositories or retention enemas, e.g., containing conventional suppository bases such as cocoa, butter or other glycerides. In addition to the formulations described previously, a compound of the invention may also be formulated as depot preparation. Such long acting formulations may be administered by implantation (for example, subcutaneously or intramuscularly) or by intramuscular injection. Thus, for example, a compound of the invention may be formulated with suitable polymeric or hydrophobic materials (for example, as an emulsion in an acceptable oil) or ion exchange resins, or as sparingly soluble derivatives, for example, as a sparingly soluble salt.

When a compound of the invention is acidic, it may be included in any of the above-described formulations as the free acid, a pharmaceutically acceptable salt, a solvate or hydrate. Pharmaceutically acceptable salts substantially retain the activity of the free acid, may be prepared by reaction with bases and tend to be more soluble in aqueous and other protic solvents than the corresponding free acid form.

4.7 Methods of Use and Doses

A compound of the invention, or compositions thereof, will generally be used in an amount effective to achieve the intended purpose. For use to treat or prevent obesity and associated co-morbid diseases and/or disorders the compounds of Formulae (I), (II), (III) or (IV) and compositions containing a compound of Formulae (I), (II), (III) or (IV) are administered or applied in a therapeutically effective amount.

The amount of a compound of the invention that will be effective in the treatment of a particular disorder or condition disclosed herein will depend on the nature of the disorder or condition, and can be determined by standard clinical techniques known in the art as previously described. In addition, in vitro or in vivo assays may optionally be employed to help identify optimal dosage ranges. The amount of a compound of the invention administered will, of course, is dependent on, among other factors, the subject being treated, and the weight of the subject, the severity of the affliction, the manner of administration and the judgment of the prescribing physician. For example, the dosage may be delivered in a pharmaceutical composition by a single administration, by multiple applications or controlled release. In a preferred embodiment, the compounds of the invention are delivered by oral sustained release administration. Preferably, in this embodiment, the compounds of the invention are administered twice per day (more preferably, once per day). Dosing may be repeated intermittently, may be provided alone or in combination with other drugs and may continue as long as required for effective treatment of the disease state or disorder.

The compounds and/or compositions containing compound(s), of structural Formulae (I)-(IV) for the pharmacological treatment of obesity and related co-morbid indications may be administered in the range 0.1 mg to 500 mg preferably 1 mg to 100 mg per day given in one or more doses and more preferably 5 mg, 10 mg, 15 mg, 20 mg, 25 mg, 35 mg or 50 mg per day and most preferably 25 mg.

The compounds of the invention are preferably assayed in vitro and in vivo, for the desired therapeutic or prophylactic activity, prior to use in humans. The compounds of the invention may also be demonstrated to be effective and safe using animal model systems.

Preferably, the therapeutically effective dose of a compound of the invention described herein will provide therapeutic benefit without causing substantial toxicity. Toxicity of compounds of the invention may be determined using standard pharmaceutical procedures and may be readily ascertained by the skilled artisan. The dose ratio between toxic and therapeutic effect is the therapeutic index. A compound of the invention will preferably exhibit particularly high therapeutic indices in treating disease and disorders. The dosage of a compound of the inventions described herein will preferably be within a range of circulating concentrations that include an effective dose with little or no toxicity.

4.8 Combination Therapy

In certain embodiments of the present invention, the compounds of the invention can be used in combination therapy with at least one other therapeutic agent. The compound of the invention and the therapeutic agent can act additively or, more preferably, synergistically. In a preferred embodiment, composition comprising a compound of the invention is administered concurrently with the administration of another therapeutic agent, which can be part of the same composition. In another embodiment, a composition comprising a compound of the invention is administered prior or subsequent to administration of another therapeutic agent.

5. EXAMPLES

The invention is further defined by reference to the following examples, which describe in detail preparation of compounds and compositions of the invention and assays for using compounds and compositions of the invention. It will be apparent to those skilled in the art that many modifications, both to materials and methods, may be practiced without departing from the scope of the invention.

In the examples below, the following abbreviations have the following meanings. If an abbreviation is not defined, it has its generally accepted meaning.

AcOH=Acetic acid
Atm=Atmosphere
Cbz=carbobenzyloxy
DCM=dichloromethane
DMAP=4-N,N-dimethylaminopyridine
DMF=N,N-dimethylformamide
DMSO=dimethylsulfoxide
g=gram
h=hours
L=liter
LC/MS=liquid chromatography/mass spectroscopy
M=molar
mL=milliliter
mmol=millimols
TBS=tert-butyldimethylsilyl
TEA=triethylamine
THF=tetrahydrofuran
TFA=trifluoroacetic acid

Example 1

General Procedure for Synthesis of 49a-d (Scheme 7)

The phenylcyclobutanenitriles 49a-d were prepared according to the protocol reported by Butler and Polatz (J. Org. Chem. 1971, 36, 1308). To a stirred suspension of sodium hydride (NaH) (0.1 mole, 2.4 g) in 25 mL of anhydrous tetrahydrofuran (THF) under nitrogen atmosphere at ice-bath temperature was dropwise added a solution of 1,3-dibromopropane (11.10 g, 0.055 mole) and appropriate benzylnitrile 47a-d (0.05 mole) in 50 mL of THF. The resulting mixture was slowly warmed to room temperature and continued stirring overnight (12 hours) at room temperature. The progress of the reaction was monitored by thin layer chromatography (TLC). The reaction was poured onto crushed ice (200 g) and then, extracted with ethyl acetate (100 mL×3). The combined extract was washed with water (100 mL×2), dried over magnesium sulfate ($MgSO_4$) and evaporated under reduced pressure to give the corresponding phenylcyclobutanenitriles 49a-d which were purified by silica gel column chromatography technique using 0-50% gradient of ethyl acetate and hexane in good yields. The pure products 49a-d gave satisfactory $^1$H NMR and/or Mass spectral data.

1-(4-Chlorophenyl)cyclobutanecarbonitrile (49a)

Colorless oil (7.60 g, 79%). It was also purchased from commercial source, Aldrich. $^1$H NMR data of the synthesized 49a is in agreement with the reported values and also the data matches with the values obtained from the commercial compound.

1-[(4-tert-butyldimethylsilyloxy)phenyl]cyclobutanecarbonitrile (49b)

Colorless oil (10.30 g, 72%). $^1$H NMR (400 MHz, $CDCl_3$): δ 0.01 (6H, s); 0.78 (9H, s); 1.86 (2H, m); 2.37 (2H, m); 2.59 (2H, m); 6.50 (2H, d, J=7.5 Hz); 7.05 (2H, d, J=7.5 Hz). MS (ESI): m/z=575.40 (M×2+H$^+$).

1-[(4-Benzyloxy)phenyl]cyclobutanecarbonitrile (49c)

Colorless oil (8.55 g, 65%). $^1$H NMR (300 MHz, $CDCl_3$): δ 2.02 (2H, m); 2.25 (2H, m); 2.81 (2H, m); 5.08 (2H, s); 6.95 (2H, broad d); 7.32 (7H, m).

1-[4-(4-methoxybenzyloxy)phenyl]cyclobutanecarbonitrile (49d)

Yellow solid (8.90 g, 61%). $^1$H NMR (400 MHz, $CDCl_3$): δ 2.03 (2H, m); 2.59 (2H, m); 2.78 (2H, m); 3.80 (3H, s); 5.97 (2H, s); 6.94 (4H, m); 7.33 (4H, m).

Example 2

General Procedure for Synthesis of 52a-d (Scheme 7)

To a stirred solution of 2M isobutyl magnesium bromide in diethyl ether (0.04 mole, 20 mL) under nitrogen atmosphere at room temperature was dropwise added a solution of appropriate cyclobutanenitrile 49a-d (0.025 mole) in 20 mL of anhydrous THF or toluene. The resulting mixture was refluxed for 18-24 hours. The progress of the reaction was monitored by TLC. In a separate round bottom flask 25 mL of anhydrous isopropanol was taken and sodium borohydride (3.00 g, 0.08 mole) was added to isopropanol portion-wise at room temperature. After having stirred for 10 minutes, the Grignard adduct from the reaction flask was directly added into the stirred solution sodium borohydride in isopropanol under nitrogen atmosphere. The resulting mixture was refluxed for 12 to 18 hours. The progress of the reaction was monitored by TLC. The reaction mixture was slowly poured onto a mixture of crushed ice (200 g) and sodium bicarbonate (5.00 g). The mixture was extracted with ethyl acetate (100 mL×3). The combined extract was washed with brine (100 mL×2), dried over sodium sulfate ($Na_2SO_4$) and evaporated under reduced pressure to give the corresponding phenylcyclobutane amines 52a-d which were purified by silica gel column chromatography technique using 0-100% gradient of ethyl acetate and hexane in good yields. The pure amine 52a-d gave satisfactory $^1$H NMR and mass spectral data.

1-[1-(4-Chlorophenyl)cyclobutyl]-3-methylbutan-1-amine (52a)

Colorless oil (5.60 g, 89%). $^1$H NMR (400 MHz, $CDCl_3$): δ 0.77 (3H, d, J=4 Hz); 0.84 (3H, d, J=4 Hz); 1.60 (2H, m); 1.75 (1H, m); 1.90 (2H, m); 2.11 (2H, m); 2.55 (4H, m); 2.94 (1H, m); 7.01 (2H, d, J=4.1 Hz); 7.19 (2H, d, J=4.1 Hz).

4-[1-(1-Amino-3-methylbutyl)cyclobutyl]phenol (52b)

The compound 52b was prepared from the intermediate 67 described in the Step 2 of Example 11 (Scheme 11). The compound 67 was treated with trifluoroacetic acid in dichloromethane at room temperature for 8 hours as described in the procedure for synthesis of compound 70 in the Step 4 of Example 11 (Scheme 11). The compound was isolated as light yellow color liquid in 73% yield. $^1$H NMR (400 MHz, $CDCl_3$): δ 0.78 (3H, broad s); 0.84 (3H, broad s); 1.61 (1H, m); 1.83 (2H, m); 1.93 (2H, m); 2.28 (2H, m); 2.45 (2H, m); 2.67 (2H, m); 3.22 (1H, m); 6.73 (2H, d, J=4 Hz); 7.14 (2H, d, J=4 Hz). MS (ESI): m/z=234.10 (M+H$^+$).

1-[1-(4-tert-Butyldimethylsilyloxy)phenyl)cyclobutyl]-3-methylbutan-1-amine (52c)

Colorless oil (6.80 g, 79%). $^1$H NMR (400 MHz, $CDCl_3$): δ 0.25 (6H, s); 0.69 (3H, d, J=4 Hz); 0.77 (3H, d, J=4 Hz); 0.82 (9H, s); 1.54 (3H, m); 1.65 (2H, m); 1.78 (2H, m); 2.00 (2H, m); 2.17 (2H, m); 2.80 (1H, m); 6.60 (2H, d, J=4 Hz); 6.82 (2H, d, J=4 Hz). MS (ESI): m/z=348.10 (M+H$^+$).

1-[1-(4-(benzyloxy)phenyl)cyclobutyl]-3-methylbutan-1-amine (52d)

Colorless oil (5.25 g, 65%). $^1$H NMR (300 MHz, $CDCl_3$): δ 0.90 (3H, d, J=4 Hz); 0.96 (3H, d, J=4 Hz); 1.61 (3H, m); 2.09 (2H, m); 2.21 (2H, m); 2.58 (2H, m); 2.80 (3H, m); 5.09 (2H, s); 6.90 (2H, broad d); 7.34 (3H, m); 7.01 (4H, m).

1-[1-(4-(4-Methoxybenzyloxy)phenyl)cyclobutyl]-3-methylbutan-1-amine (52e)

Colorless oil (5.00 g, 57%). $^1$H NMR (300 MHz, $CDCl_3$): δ 0.88 (3H, d, J=4 Hz); 0.94 (3H, d, J=4 Hz); 1.69 (3H, m); 1.98 (2H, m); 2.18 (1H, m); 2.36 (4H, m); 3.00 (1H, m); 3.77 (3H, s); 5.31 (2H, s); 6.71-7.01 (8H, m). MS (ESI): m/z=354.00 (M+H$^+$).

Example 3

General Procedure for Synthesis of 54a-e (Scheme 7)

To a stirred suspension of cesium carbonate (Cs$_2$CO$_3$) (1.30 g, 0.004 Mole) in 20 mL of anhydrous N,N-dimethylformamide (DMF) under nitrogen atmosphere at room temperature was added tetrabutylammonium iodide (TBAI) (1.47 g, 0.004 mole) followed by appropriate cyclobutane amine 52a-d (0.0035 mole). After having stirred for 30 minutes, a solution of appropriate bromoalkylcarboxylic esters 53 in 5 mL of DMF was introduced into the reaction mixture dropwise. The resulting mixture was stirred for 18-24 hours and the progress of the reaction was monitored by TLC. The reaction mixture was diluted with ethyl acetate (50 mL), filtered through a CELITE® pad and washed the CELITE® pad with ethyl acetate (15 mL×3). The combined filtrate was washed with brine (50 mL), water (50 mL), dried over sodium sulfate (Na$_2$SO$_4$) and evaporated. The residue was purified by silica gel column chromatography technique using 0-50% gradient of ethyl acetate and hexane to give the corresponding amine 54 in good yield. The cyclobutane amines 54a-e gave satisfactory $^1$H NMR and mass spectral data.

Ethyl 2-(1-(1-(4-chlorophenyl)cyclobutyl)-3-methylbutylamino]acetate (54a)

Colorless oil (0.69 g, 59%). $^1$H NMR (400 MHz, CDCl$_3$): δ 0.80 (3H, d, J=4 Hz); 0.84 (3H, d, J=4 Hz); 1.25 (3H, t, J=4.25 Hz); 1.60 (2H, m); 1.78 (1H, m); 2.19 (2H, m); 2.27 (2H, m); 2.36 (2H, m); 2.75 (1H, m); 3.48 (2H, s); 4.16 (2H, q, J=4.25 Hz); 7.16 (2H, d, J=4 Hz); 7.23 (2H, d, J=4 Hz). MS (ESI): m/z=338.00 (M+H$^+$)

Ethyl 2-(1-(1-(4-chlorophenyl)cyclobutyl)-3-methylbutylamino]butanoate (54b)

Colorless oil (1.10 g, 84%). $^1$H NMR (400 MHz, CDCl$_3$): δ 0.82 (3H, d, J=4 Hz); 0.85 (3H, d, J=4 Hz); 1.24 (3H, t, J=4.25 Hz); 1.60 (2H, m); 1.71 (3H, m); 1.88 (2H, m); 2.02 (1H, broad s); 2.15 (2H, m); 2.23 (2H, m); 2.38 (2H, m); 2.76 (3H, m); 4.10 (2H, q, J=4.25 Hz); 7.14 (2H, d, J=4 Hz); 7.24 (2H, d, J=4 Hz). MS (ESI): m/z=366.20 (M+H$^+$)

Isopropyl 2-(1-(1-(4-chlorophenyl)cyclobutyl)-3-methylbutylamino]butanoate (54c)

Colorless oil (1.05 g, 80%). $^1$H NMR (300 MHz, CDCl$_3$): δ 0.83 (3H, broad s); 0.85 (3H, broad s); 1.24 (3H, broad s); 1.26 (3H, broad s); 1.67 (3H, m); 1.94 (4H, m); 2.00 (3H, m); 2.21 (4H, m); 2.36 (3H, m); 2.85 (1H, m); 5.02 (1H, m); 7.05 (2H, broad d); 7.29 (2H, broad d). MS (ESI): m/z=382.10 (M+H$^+$)

Isobutyl 2-(1-(1-(4-chlorophenyl)cyclobutyl)-3-methylbutylamino]butanoate (54d)

Colorless oil (1.15 g, 83%). $^1$H NMR (300 MHz, CDCl$_3$): δ 0.94 (6H, broad s); 0.97 (6H, broad s); 1.61 (2H, m); 1.76 (2H, m); 1.94 (4H, m); 2.20 (3H, m); 2.42 (2H, m); 2.53 (2H, m); 2.80 (1H, m); 3.87 (2H, broad d); 7.16 (2H, broad d); 7.27 (2H, broad d). MS (ESI): m/z=394.20 (M+H$^+$).

Benzyl 2-(1-(1-(4-chlorophenyl)cyclobutyl)-3-methylbutylamino]butanoate (54e)

Colorless oil (1.13 g, 76%). $^1$H NMR (300 MHz, CDCl$_3$): δ 0.80 (3H, d, J=4 Hz); 0.85 (3H, d, J=4 Hz); 1.58 (1H, m); 1.73 (2H, m); 1.84 (2H, m); 2.18 (4H, m); 2.33 (1H, m); 2.49 (4H, m); 2.72 (2H, m); 3.44 (1H, m); 5.11 (2H, broad s); 7.13 (2H, d, J=5.25 Hz); 7.24 (2H, d, J=5.25 Hz); 7.33 (5H, m). MS (ESI): m/z=428.30 (M+H$^+$).

Ethyl 2-(1-(1-(4-chlorophenyl)cyclobutyl)-3-methylbutylamino]pentanoate (54f)

Colorless oil (1.17 g, 88%). $^1$H NMR (400 MHz, CDCl$_3$): δ 0.81 (3H, d, J=4 Hz); 0.86 (3H, d, J=4 Hz); 1.24 (3H, t, J=4.5 Hz); 1.47 (2H, m); 1.60 (2H, m); 1.78 (3H, m); 1.88 (4H, m), 2.31 (3H, m); 2.78 (2H, m); 3.17 (1H, m); 4.12 (2H, q, J=4.25 Hz); 7.14 (2H, d, J=5 Hz); 7.23 (2H, d, J=5 Hz). MS (ESI): m/z=380.3 (M+H$^+$).

Example 4

Alternate Route for the Synthesis of 54a (Scheme 8)

To a stirred solution of cyclobutane amine 52a (0.68 g, 0.0027 mole) and ethyl glyoxylate (50% solution in toluene) (1.02 g, 0.01 mole) in 20 mL of a mixture of solvents DMF and acetic acid (ratio, 99:1) was added sodium triacetoxyborohydride (2.11 g, 0.01 mole) portion-wise over a period of 15 minutes at room temperature. The resulting mixture was stirred for 8 hours at room temperature and the progress of the reaction was monitored by TLC. The reaction mixture was poured in to saturated sodium bicarbonate solution (50 mL) and extracted with ethyl acetate (50 mL×3). The combined extract was washed with water (50 mL), dried over sodium sulfate (Na$_2$SO$_4$) and evaporated. The residue was purified by silica gel column chromatography using 0-50% gradient of ethyl acetate and hexane as eluents to give pure 54a as colorless liquid in 45% (0.41 g) yield. The $^1$H NMR and mass spectral data are identical to the compound synthesized using the protocol described for the synthesis of 54a-e (Example 3, Scheme 7).

Example 5

Alternate route for the synthesis of 54f (Scheme 8)

Step 1. To a stirred solution of cyclobutane amine 52a (2.51 g, 0.01 mole) in 50 mL of methanol was added benzaldehyde (1.27 g, 0.012 mole) under nitrogen atmosphere at room temperature. After having stirred for 2 hours at room temperature the reaction mixture was cooled to 0° C. and then, added sodium borohydride (NaBH$_4$) (0.55 g, 0.15 mole) portion-wise over a period of 20 min. The reaction mixture was stirred for 5 hours and the progress of the reaction was monitored by TLC. The reaction mixture was concentrated under vacuum and the residue was diluted with ethyl acetate (100 mL). The resulting mixture was washed successively with saturated sodium bicarbonate solution (50 mL), water (50 mL×2), dried over sodium sulfate (Na$_2$SO$_4$) and evaporated. The residue was purified by silica gel column chromatography using 0-50% gradient of ethyl acetate and hexane to give the corresponding N-benzyl amine 57 in 90% (3.06 g) yield. The amine 57 gave satisfactory $^1$H NMR (300 MHz, CDCl$_3$): δ 0.82 (3H, broad s); 0.85 (3H, broad s); 1.03-1.34 (3H, m); 1.67-1.88 (3H, m); 2.16-2.46 (4H, m); 2.87 (1H, m); 3.92 (2H, s); 7.24-7.34 (9H, m).

Step 2. To a stirred solution of N-benzylamine 57 (2.56 g, 0.0075 mole) in anhydrous THF (25 mL) was added a 10 M solution of n-butyllithium (n-BuLi) (0.8 mL, 0.008 mole) in hexanes under nitrogen atmosphere at −78° C. The resulting mixture was warmed up to 0° C. The reaction mixture was cooled to −78° C. again and then, added dropwise a solution of ethyl 5-bromovalerate (3.13 g, 0.01 mole) in THF (10 mL). The reaction mixture was slowly warmed to room temperature and continued stirring at room temperature for 5 hours. The progress of the reaction was monitored by TLC. The reaction mixture was poured onto crushed ice (100 g) and extracted with ethyl acetate (50 mL×3). The combined extract was washed with water (100 mL), dried over sodium sulfate ($Na_2SO_4$) and evaporated. The residue was purified by silica gel column chromatography using 0-50% gradient of ethyl acetate and hexane as eluent to give the corresponding amine 58 in 69% (2.43 g) yield. The amine 58 gave satisfactory $^1$H NMR (300 MHz, $CDCl_3$): δ 0.84 (3H, broad d); 0.87 (3H, broad d); 1.25-1.46 (7H, m); 1.50-2.00 (6H, m); 2.34 (4H, m); 3.09 (1H, broad s); 3.89 (2H, s); 4.14 (2H, broad q); 6.78-7.09 (4H, m); 7.35 (5H, m).

Step 3. To a stirred suspension of 10% palladium on carbon (Pd—C) (0.5 g) was added a solution of 58 (1.17 g, 0.0025 mole) in ethyl acetate (25 mL) followed by few drops of concentrated hydrochloric acid (HCl). The resulting mixture was stirred under hydrogen gas atmosphere for 12 hours at atmospheric pressure and the progress of the reaction was monitored by TLC. The reaction mixture was filtered and the precipitate was washed with a 1:1 mixture of ethyl acetate and ethanol (15 mL×3). The combined filtrate was concentrated under reduced pressure and the residue was purified by silica gel column chromatography using 0-50% gradient of ethyl acetate and hexane as eluent to give the pure aminoester 54f in 81% (0.77 g) good yield. The aminoester 54f gave satisfactory $^1$H NMR and mass spectral data and they are identical to the compound prepared using the general procedure described in Example 3 (Scheme 7).

Example 6

Synthesis of 4-chlorobenzylnitrile 47a

The building block 47a was purchased from commercial source, Aldrich. However, 9a can also be prepared in good yields from the literature methods in good as described herein for 47b.

Example 7

Synthesis of 2-[4-(benzyloxy)phenyl]acetonitrile (47b) (Scheme 9)

To a stirred suspension of potassium carbonate ($K_2CO_3$) (7 g, 0.05 mole) in anhydrous DMF (50 mL) was added 4-hydroxybenzylnitile (59) (6.65 g, 0.05 mole) followed by benzylbromide (8.55 g, 0.05 mole). The resulting mixture was heated at 70° C. for 10-12 hours and the progress of the reaction was monitored by TLC. The reaction mixture was diluted with ethyl acetate (100 mL) and filtered. The filtrate was washed with water (100 mL×2), dried over magnesium sulfate ($MgSO_4$) and evaporated under reduced pressure. The residue was purified by silica gel column chromatography using 0-50% gradient of ethyl acetate and hexane as eluents to give the pure 4-benzyloxybenzylnitrile (47b) as white solid in good 88% (9.82 g) yield. The pure 47b gave satisfactory $^1$H and mass spectral data. $^1$H NMR (300 MHz, $CDCl_3$): δ 3.70 (2H, s); 5.08 (2H, s); 6.98 (2H, broad s); 7.23 (2H, broad s); 7.40 (5H, m). MS (ESI): m/z=223.10 (M+H$^+$)

Example 8

Synthesis of 4-(4-methoxybenzyloxy)benzylnitrile (47c) (Scheme 9)

4-(4-Methoxybenzyloxy)benzylnitrile (47c) was prepared by following the protocol described for the synthesis of 47b in 76% (9.60 g).

Example 9

Synthesis of 2-[4-(tert-butyldimethylsilyloxy)phenyl]acetonitrile (47d) (Scheme 9)

To a stirred solution of 4-hydroxybenzylnitrile (59) (6.65 g, 0.05 mole) in 75 mL of dichloromethane (DCM) was added imidazole (3.40 g, 0.05 mole) and N,N-dimethylaminopyridine (DMAP) (1.2 g, 0.01 mole). After having stirred for 10 minutes, a solution of tert-butyldimethylsilyl chloride (8.29 g, 0.055 mole) in 50 ml of DCM was added dropwise at ice-bath temperature. The resulting mixture was stirred for 8 hours and the progress of the reaction was monitored by TLC. The reaction mixture was washed with cold water (100 mL×2), dried over magnesium sulfate ($MgSO_4$) and evaporated under reduced pressure. The residue was purified by silica gel column chromatography using 0-25% gradient of ethyl acetate and hexane as eluents to give the pure 47d as colorless thick liquid in 97% (12.58 g) yield. The pure 47d gave satisfactory $^1$H and mass spectral data. $^1$H NMR (400 MHz, $CDCl_3$): δ 0.00 (6H, s); 0.78 (9H, s); 3.47 (2H, s); 6.55 (2H, d, J=5.2 Hz); 6.97 (2H, d, J=5.2 Hz).

Example 10

Synthesis of 1-[1-(4-chlorophenyl)cyclobutyl]-3-(1,3-dioxan-2-yl)propan-1-amine (65) (Scheme 10)

The cyclobutanealkyl amine 65 was prepared in good yields by following the protocol described for 52a-d in Scheme 7. Colorless oil (79%). $^1$H NMR (400 MHz, $CDCl_3$): δ 1.53-1.85 (6H, m); 1.90-2.06 (2H, m); 2.20-2.34 (6H, m); 2.89 (1H, m); 3.72 (2H, m); 4.05 (2H, m); 4.45 (1H, t, J=4 Hz); 7.05 (2H, d, J=5.25 Hz); 7.24 (2H, d, J=5.25 Hz). MS (ESI): m/z=310.10 (M+H$^+$).

Example 11

Synthesis of ethyl 2-[4-(1-(1-amino-3-methylbutyl) cyclobutyl)phenoxy]aceate (70) (Scheme 11)

Step 1. Synthesis of tert-Butyl 1-[1-(4-tert-butyldimethylsilyloxy)phenyl)cyclobutyl]-3-methylbutylcarbamate (66)

To a stirred solution of 52d (5.20 g, 0.014 mole) and triethylamine (TEA) (2 mL, 0.014 mole) in DCM (25 mL) at room temperature was added a solution of di-tert-butyl dicarbonate (BOC anhydride) (3.20 g, 0.015 mole) in DCM (25 mL). The resulting mixture was stirred at room temperature for 12 hours and the progress of the reaction was monitored by TLC. The reaction mixture was diluted with DCM (50 mL), washed with water (50 mL×3), dried over sodium sulfate ($Na_2SO_4$), and evaporated. The residue was purified by silica gel column chromatography using 0-25% gradient of ethyl acetate and hexane as eluent to get the pure N—BOC protected amine 66 as colorless liquid in 98% (6.30 g) yield. $^1$H NMR (400 MHz, $CDCl_3$): δ 0.27 (6H, s); 0.73 (3H, d, J=4

Hz); 0.80 (3H, d, J=4 Hz); 0.89 (9H, s); 1.45 (9H, broad s); 1.50-1.55 (2H, m); 1.62-1.66 (1H, m); 1.75-1.78 (2H, m); 1.91-2.05 (2H, m); 2.17 (2H, m); 3.20 (1H, m); 6.72 (2H, broad d); 6.95 (2H, broad d). MS (ESI): m/z=348.10 (M-BOC).

Step 2. Synthesis of tert-Butyl 1-[1-(4-hydroxyphenyl)cyclobutyl]-3-methylbutyl-carbamate (67)

The deprotection of OTBs group was carried out by following a literature protocol (Maiti, G. and Roy, S. C., Tetrahedron Letters 1997, 38, 495). A stirred solution of N—BOC protected amine 66 (2.29 g, 0.005 mole) in 20 mL of a mixture of dimethylsulfoxide and water (95:5 ratio) was heated at 90° C. for 6 hours. The progress of the reaction was monitored by TLC. The reaction mixture was diluted with ethyl acetate (100 mL) and then, successively washed with brine (50 mL), water (50 mL). The organic layer was dried over sodium sulfate ($Na_2SO_4$) and evaporated. The residue was purified by silica gel column chromatography using 0-50% gradient of ethyl acetate and hexane as eluent to give the pure phenolic derivative 67 as colorless liquid in 79% (1.31 g) yield. $^1$H NMR (400 MHz, $CDCl_3$): δ 0.78 (3H, broad s); 0.80 (3H, broad s); 1.70 (9H, broad s); 1.52-1.69 (3H, m); 2.24 (2H, m); 2.43 (2H, m); 2.78 (2H, m); 3.40 (1H, m); 6.69 (2H, broad d); 7.09 (2H, broad d). MS (ESI): m/z=667.00 (2×M+H$^+$).

Step 3. Synthesis of ethyl 2-[4-(1-(1-(tert-butoxycarbonylamino)-3-methylbutyl)-cyclobutyl)phenoxy]-aceate (69)

To a stirred solution of phenol 67 (0.5 g, 0.0015 mole) in 25 mL of anhydrous DMF was added cesium carbonate ($Cs_2CO_3$). The resulting mixture was heated at 70° C. for 12 hours. The reaction mixture was cooled to room temperature and added ethyl bromoacetate. The reaction mixture was further stirred at 70° C. for 8 hours and the progress of the reaction was monitored by TLC. The reaction mixture was diluted with ethyl acetate (100 mL), washed with water (50 ML×2), dried over anhydrous sodium sulfate ($Na_2SO_4$) and evaporated. The residue was purified by silica gel column chromatography using 0-50% gradient of ethyl acetate and hexane as eluent to give the pure ester 69a as colorless liquid in 61% (0.38 g) yield. MS (ESI): m/z=420.00 (M+H$^+$).

Step 4. Synthesis of ethyl 2-[4-(1-(1-amino-3-methylbutyl)cyclobutyl)phenoxy]aceate (70)

A solution of 69a (0.25 g, 0.0005 mole) in 20 mL of 1:1 mixture of DCM and trifluoroacetic acid (TFA) was stirred at room temperature for 8 hours. The progress of the reaction was monitored by TLC. The reaction mixture was concentrated under reduced pressure. The residue was diluted with DCM (50 mL), washed with brine (25 mL), dried over sodium sulfate ($Na_2SO_4$) and evaporated. The residue was purified by 0-100% gradient of ethyl acetate and hexane as eluent to give the pure amine 70a as colorless oil in 85% (0.13 g) yield. $^1$H NMR (400 MHz, $CDCl_3$): δ 0.85 (3H, broad s); 0.83 (3H, broad s); 1.25 (3H, t, J=4.5 Hz); 1.59 (1H, m); 1.85 (2H, m,); 1.93 (2H, m); 2.20 (2H, m); 2.42 (2H, m); 2.68 (2H, m); 3.21 (1H, m); 4.08 (2H, q, J=4.5 Hz); 5.09 (2H, s); (6.81 (2H, broad d); 7.13 (2H, broad d).

Example 12

In vitro Pharmacology Results

The monoamine transporters inhibitory activities of selected compounds (54b and 54d) are reported herein. The compounds were evaluated at MDS Pharma services (22011 Drive SE, Bothell, Wash. 98021, USA) using well established radioligand binding assays protocols (Galli, A. et al., J. Exp. Biol. 1995, 198, 2197-2212; Giros, B. et al., Trends Pharmcol. Sci. 1993, 14, 43-49; Gu, H. et al., J. Biol. Chem. 1994, 269(10), 7124-7130; Shearman, L. P. et al, Am. J. Physiol., 1998, 275(6 Pt 1), C1621-1629; Wolf, W. A. et al., J. Biol. Chem. 1992, 267(29), 20820-20825). The human recombinant transporter proteins dopamine (DAT), norepinephrine (NET) and serotonin (SERT) were selected for the in vitro assays. The CHO-K1 cells expressed with human recombinant dopamine transporter (DAT) (MDS catalog 220320) was used for evaluating the dopamine transporter inhibitory activity. Whereas, MDCK cells expressed with human recombinant transporters norepinephrine (NET) (MDS catalog no. 204410) and serotonin (SERT) (MDS catalog no. 274030) were used for evaluating the norepinephrine transporter (NET) and serotonin transporter (SERT) inhibitory activities, respectively. The radioligand binding assays were carried out at four different test concentrations and the test concentrations were 1 nM, 10 nM, 0.1 μM, and 1 μM.

The assays were carried out in duplicates and the quantitative data are reported as IC50, Ki, and nH. Where presented, $IC_{50}$ values were determined by a non-linear, least squares regression analysis using MathIQ™ (ID Business Solutions Ltd. UK). Where inhibition constants (Ki) are presented, the Ki values were calculated using the equation of Cheng and Prusoff (Cheng, Y., Prusoff, W. H., Biochem. Pharmacol. 1973, 22:3099-3108) using the observed $IC_{50}$ of the tested compound, the concentration of radioligand employed in the assay and the historical values for the $K_D$ of the ligand (obtained experimentally at MDS Pharma Services). Where presented, the Hill coefficient ($n_H$), defining the slope of the competitive binding curve, was calculated using MathIQ™.

The monoamine transporters inhibitory activities of selected compounds (54b and 54d) using radioligand binding assays are reported in following table.

| Compound | Assay | IC50 | Ki | $n_H$ |
|---|---|---|---|---|
| 54b | DAT | 0.0569 μM | 0.0452 μM | 0.826 |
| 54b | NET | 0.121 μM | 0.120 μM | 0.832 |
| 54b | SERT | 0.140 μM | 0.0228 μM | 0.677 |
| 54d | DAT | 0.370 μM | 0.294 μM | 0.943 |
| 54d | NET | 0.182 μM | 0.180 μM | 1.04 |
| 54d | SERT | 0.415 μM | 0.0676 μM | 0.578 |

All printed patents and publications referred to in this application are hereby incorporated herein in their entirety by this reference.

While the preferred embodiment of the invention has been illustrated and described, it will be appreciated that various changes can be made therein without departing from the spirit and scope of the invention.

What is claimed is:

1. A cycloalkylmethylamine derivative of structural Formula (IV):

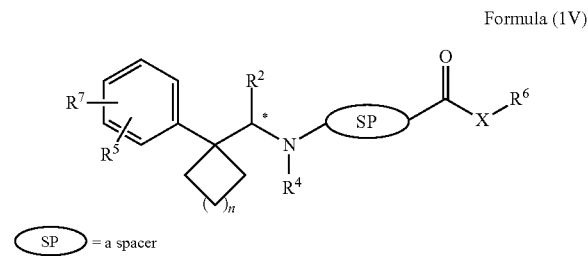

Formula (IV)

or a pharmaceutically acceptable salt thereof, wherein:
n is 1;
SP is a spacer of alkylene or a direct bond;
X is O or NH;
$R^2$ is hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, or substituted heteroarylalkyl;
$R^4$ is hydrogen, alkyl, or substituted alkyl;
$R^5$ is hydrogen, alkyl, halogen, hydroxyl, or alkoxy;
$R^6$ is hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, or substituted heteroarylalkyl; and
$R^7$ is hydrogen, alkyl, halogen, hydroxyl, or alkoxy.

2. The cycloalkylmethylamine derivative of claim 1, wherein SP is alkylene.

3. The cycloalkylmethylamine derivative of claim 1, wherein SP is a direct bond.

4. The cycloalkylmethylamine derivative of claim 2, wherein X is O.

5. The cycloalkylmethylamine derivative of claim 3, wherein X is O.

6. The cycloalkylmethylamine derivative of claim 2, wherein X is NH.

7. The cycloalkylmethylamine derivative of claim 3, wherein X is NH.

8. The cycloalkylmethylamine derivative of claim 1, wherein $R^4$ is H.

9. The cycloalkylmethylamine derivative of claim 1, wherein $R^5$ is H or alkyl.

10. The cycloalkylmethylamine derivative of claim 1, wherein $R^5$ is alkoxy.

11. The cycloalkylmethylamine derivative of claim 1, wherein $R^5$ is halogen.

12. The cycloalkylmethylamine derivative of claim 1, wherein $R^6$ is alkyl or substituted alkyl.

13. The cycloalkylmethylamine derivative of claim 1, wherein $R^7$ is H or alkyl.

14. The cycloalkylmethylamine derivative of claim 1, wherein $R^7$ is alkoxy or halogen.

15. The cycloalkylmethylamine derivative of claim 1, wherein $R^2$ is ethyl, n-propyl, iso-propyl or n-butyl, s-butyl, or t-butyl.

16. The cycloalkylmethylamine derivative of claim 1, wherein said derivative is Compound 67

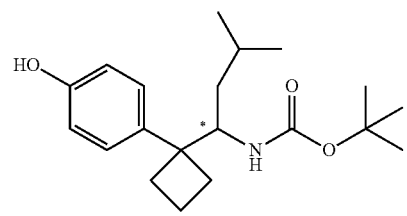

17. The cycloalkylmethylamine derivative of claim 1, wherein said derivative is Compound 58

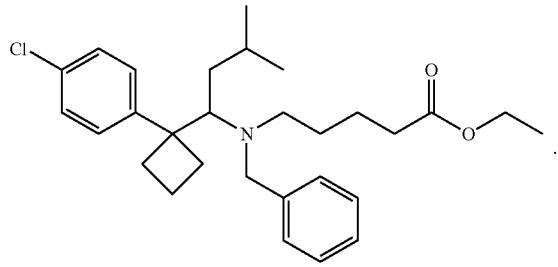

18. A method of treating obesity, comprising administering to a subject the cycloalkylmethylamine derivative according to claim 2.

19. A method of treating obesity, comprising administering to a subject the cycloalkylmethylamine derivative according to claim 3.

20. A method of treating depression, comprising administering to a subject the cycloalkylmethylamine derivative according to claim 1.

* * * * *